United States Patent
Young et al.

(10) Patent No.: US 9,023,072 B2
(45) Date of Patent: *May 5, 2015

(54) MECHANISM FOR ASSEMBLY OF ULTRASONIC INSTRUMENT

(71) Applicant: Ethicon Endo-Surgery, Inc., Cincinnati, OH (US)

(72) Inventors: Joseph E. Young, Loveland, OH (US); David A. Witt, Maineville, OH (US); Reginald D. Fortson, Cincinnati, OH (US); Thomas E. Adams, Loveland, OH (US); John A. Weed, III, Monroe, OH (US); William D. Dannaher, Suzhou (CN)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,484

(22) Filed: Apr. 8, 2013

(65) Prior Publication Data

US 2013/0338691 A1 Dec. 19, 2013

Related U.S. Application Data

(60) Continuation of application No. 13/525,808, filed on Jun. 18, 2012, now Pat. No. 8,435,258, which is a division of application No. 11/751,733, filed on May 22, 2007, now Pat. No. 8,366,727.

(60) Provisional application No. 60/809,971, filed on Jun. 1, 2006.

(51) Int. Cl.
*A61B 17/32* (2006.01)
*B25B 23/142* (2006.01)

(52) U.S. Cl.
CPC . *A61B 17/320068* (2013.01); *A61B 17/320092* (2013.01); *B25B 23/142* (2013.01)

(58) Field of Classification Search
CPC .......... A61B 17/32; A61B 17/320068; A61B 17/320092; A61B 2017/320072; A61B 2017/320076; A61B 2017/32008; A61B 2017/320084; A61B 2017/320088; A61B 2017/320096; B25B 23/14; B25B 23/141; B25B 23/142; B25B 23/147
USPC ....................... 604/22; 606/169; 81/429, 467, 81/473–477, 480, 481
See application file for complete search history.

(56) References Cited

U.S. PATENT DOCUMENTS

| 1,080,554 A | 12/1913 | Hopkins |
| 2,708,437 A | 5/1955 | Hutchins |

(Continued)

FOREIGN PATENT DOCUMENTS

| DE | 20314010 U1 | 1/2005 |
| EP | 0366624 A2 | 5/1990 |

(Continued)

OTHER PUBLICATIONS

European Search Report dated May 3, 2010, European Patent Application No. EP07797820.3.

(Continued)

*Primary Examiner* — Ryan Severson

(57) ABSTRACT

An ultrasonic clamp coagulator system that is configured to permit selective cutting, coagulation and clamping of tissue during surgical procedures. An elongated portion of the instrument can be configured for endoscopic applications and has an outside diameter of less than 6 mm. The system includes a one-piece torque wrench that is provided with cantilever arms aligned in an annular fashion about the centerline of the torque wrench. The cantilever arms include teeth in an inward perpendicular fashion in relation to cantilever arms. The clamp coagulator includes an outer tube retainer that includes spline gears projecting in a perpendicular fashion along the outer circumference of retainer. Torque is transmitted through the cantilever arms to the spline gears for attaching a handpiece to the clamp coagulator.

13 Claims, 19 Drawing Sheets

(56) References Cited

U.S. PATENT DOCUMENTS

| | | |
|---|---|---|
| 3,142,211 A | 7/1964 | Faso |
| 3,486,402 A | 12/1969 | Dunlap et al. |
| 4,832,021 A | 5/1989 | Kuhl et al. |
| 4,989,583 A | 2/1991 | Hood |
| 5,057,119 A | 10/1991 | Clark et al. |
| 5,059,210 A | 10/1991 | Clark et al. |
| 5,119,983 A | 6/1992 | Green et al. |
| 5,261,922 A | 11/1993 | Hood |
| 5,322,055 A | 6/1994 | Davison et al. |
| 5,334,183 A | 8/1994 | Wuchinich |
| 5,359,996 A | 11/1994 | Hood |
| 5,417,672 A | 5/1995 | Nita et al. |
| 5,449,370 A | 9/1995 | Vaitekunas |
| 5,591,143 A | 1/1997 | Trombley, III et al. |
| 5,630,420 A | 5/1997 | Vaitekunas |
| 5,776,155 A | 7/1998 | Beaupre et al. |
| 5,873,873 A | 2/1999 | Smith et al. |
| 5,921,956 A | 7/1999 | Grinberg et al. |
| 5,935,144 A | 8/1999 | Estabrook |
| 5,938,633 A | 8/1999 | Beaupre |
| 5,944,737 A | 8/1999 | Tsonton et al. |
| 5,968,061 A | 10/1999 | Mirza |
| 5,971,949 A | 10/1999 | Levin et al. |
| 5,980,510 A | 11/1999 | Tsonton et al. |
| 5,996,453 A | 12/1999 | Blacklock |
| 6,007,514 A | 12/1999 | Nita |
| 6,036,667 A | 3/2000 | Manna et al. |
| 6,129,735 A | 10/2000 | Okada et al. |
| 6,193,709 B1 | 2/2001 | Miyawaki et al. |
| 6,214,023 B1 | 4/2001 | Whipple et al. |
| 6,254,622 B1 | 7/2001 | Hood |
| 6,280,407 B1 | 8/2001 | Manna et al. |
| 6,325,811 B1 | 12/2001 | Messerly |
| 6,439,086 B1 | 8/2002 | Bahr |
| 6,468,286 B2 | 10/2002 | Mastri et al. |
| 6,499,358 B1 | 12/2002 | Hogan et al. |
| 6,660,017 B2 | 12/2003 | Beaupre |
| 6,662,693 B2 | 12/2003 | Hu |
| 6,716,028 B2 | 4/2004 | Rahman et al. |
| 6,773,444 B2 | 8/2004 | Messerly |
| 6,807,885 B2 | 10/2004 | Loper |
| 6,868,761 B2 | 3/2005 | Stoick et al. |
| 6,887,252 B1 | 5/2005 | Okada et al. |
| 6,958,070 B2 | 10/2005 | Witt et al. |
| 7,014,023 B1 | 3/2006 | Gauthier |
| 7,156,201 B2 | 1/2007 | Peshkovskiy et al. |
| 7,159,494 B2 | 1/2007 | Jamnia et al. |
| 7,163,548 B2 | 1/2007 | Stulen et al. |
| 7,247,161 B2 | 7/2007 | Johnston et al. |
| 7,430,945 B2 | 10/2008 | Gauthier et al. |
| 7,512,446 B2 | 3/2009 | Honeck |
| 7,544,200 B2 | 6/2009 | Houser |
| D617,163 S | 6/2010 | Miller et al. |
| 7,780,659 B2 | 8/2010 | Okada et al. |
| 7,799,044 B2 | 9/2010 | Johnston et al. |
| 7,846,155 B2 | 12/2010 | Houser et al. |
| 7,913,594 B2 | 3/2011 | Gauthier et al. |
| 8,057,467 B2 | 11/2011 | Faller et al. |
| 8,114,104 B2 | 2/2012 | Young et al. |
| 8,167,616 B2 | 5/2012 | Jamnia et al. |
| 8,366,727 B2 | 2/2013 | Witt et al. |
| 2004/0127926 A1 | 7/2004 | Beaupre |
| 2004/0176686 A1 | 9/2004 | Hare et al. |
| 2005/0033337 A1 | 2/2005 | Muir et al. |
| 2005/0192610 A1 | 9/2005 | Houser et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2007/0282333 A1 | 12/2007 | Fortson et al. |
| 2007/0282334 A1 | 12/2007 | Young et al. |

FOREIGN PATENT DOCUMENTS

| | | |
|---|---|---|
| EP | 0450578 B1 | 9/1996 |
| EP | 0897696 B1 | 2/1999 |
| EP | 0857547 B1 | 4/2003 |
| EP | 1649980 A1 | 4/2006 |
| GB | 2148767 A | 6/1985 |
| JP | 8-275948 A | 10/1996 |
| WO | WO 95/10233 A1 | 4/1995 |
| WO | WO 98/27875 A1 | 7/1998 |
| WO | WO 01/24713 A1 | 4/2001 |

OTHER PUBLICATIONS

European Search Report dated Dec. 7, 2010, International Application No. EP09075126.4.

European Search Report dated Dec. 9, 2010, International Application No. EP10075344.1.

Partial European Search Report dated Aug. 14, 2012, European Application No. EP12161838.3.

Supplementary European Search Report; International Application No. 07797820.3; Dated May 20, 2010.

International Search Report; International Application No. PCT/US2007/069842; Dated Jul. 14, 2008.

International Preliminary Report; International Application No. PCT/US2007/069842; Dated Dec. 18, 2008.

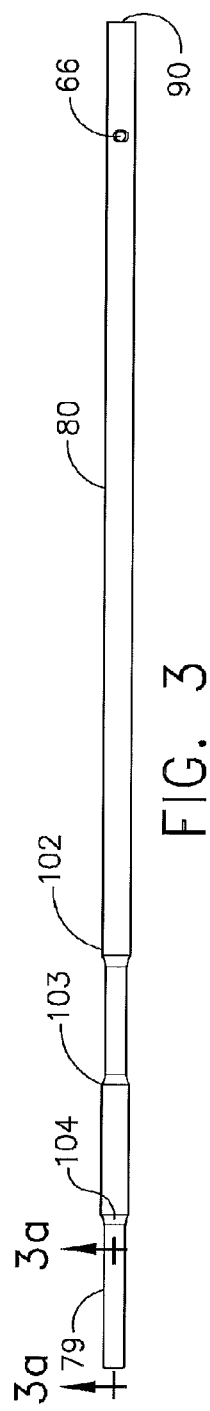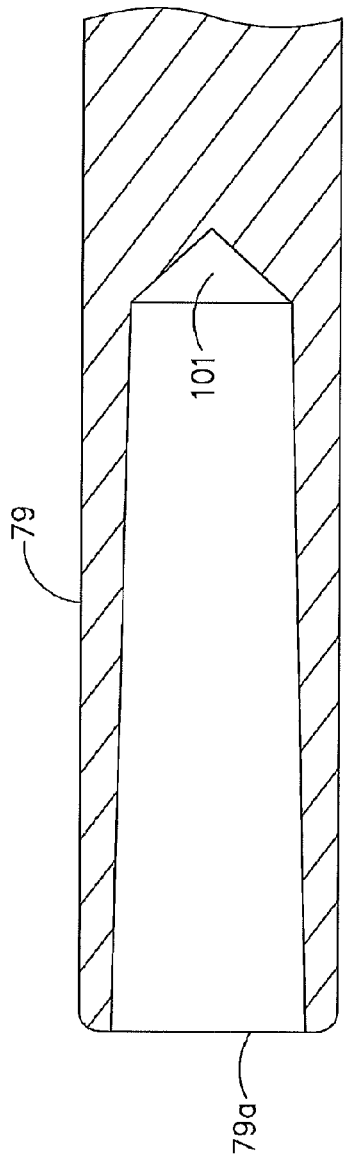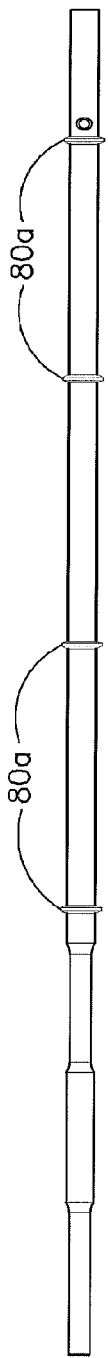

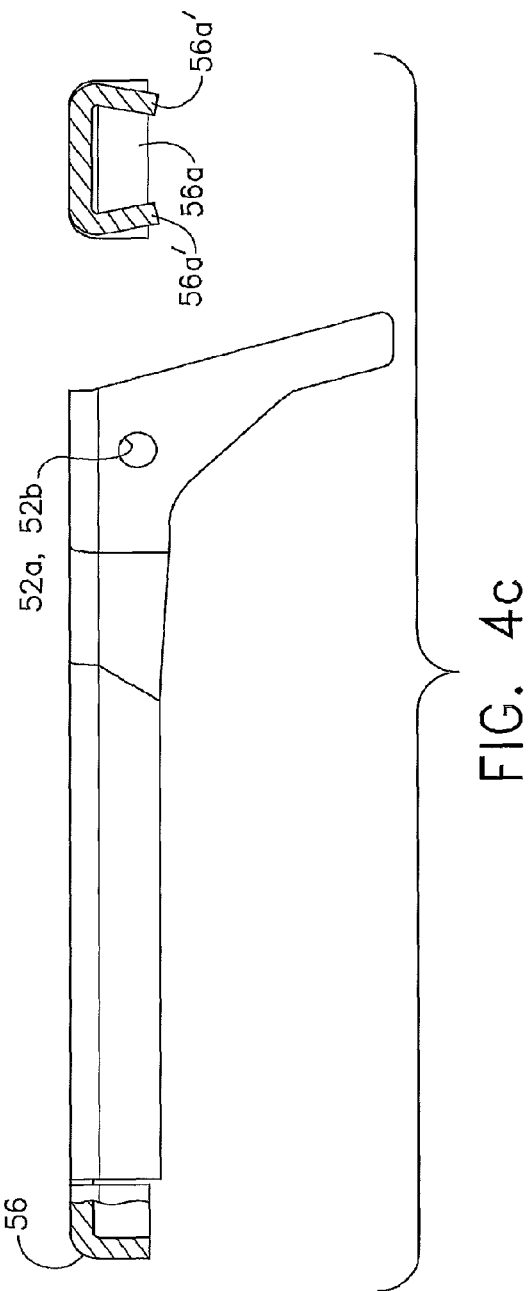
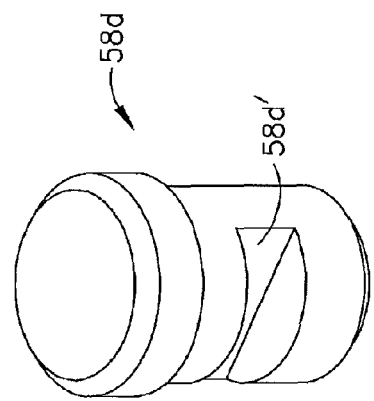

though these designs have been

MECHANISM FOR ASSEMBLY OF ULTRASONIC INSTRUMENT

REFERENCE TO RELATED APPLICATIONS

The present application is continuation of application Ser. No. 13/525,808 filed on Jun. 18, 2012 and issued as U.S. Pat. No. 8,435,258, which is a divisional of application Ser. No. 11/751,733 filed on May 22, 2007 and issued as U.S. Pat. No. 8,366,727, which claims the priority benefit of U.S. provisional patent application Ser. No. 60/809,971, filed on Jun. 1, 2006.

FIELD OF THE INVENTION

The present invention relates, in general, to ultrasonic surgical instruments and, more particularly, to an ultrasonic surgical clamp coagulator apparatus particularly configured to provide increased tissue transection forces.

BACKGROUND OF THE INVENTION

This application contains subject matter that relates to and incorporates by reference in their entirety, for any and all purposes, the following non-provisional applications:

ULTRASONIC SURGICAL BLADE AND INSTRUMENT HAVING A GAIN STEP, U.S. Pat. No. 7,163,548.

TISSUE PAD FOR USE WITH AN ULTRASONIC SURGICAL INSTRUMENT, Ser. No. 11/245,819, filed Oct. 7, 2005, abandoned;

COMBINATION TISSUE PAD FOR USE WITH AN ULTRASONIC SURGICAL INSTRUMENT, Ser. No. 11/246,794, filed Oct. 7, 2005, allowed as U.S. Pat. No. 7,544,200;

ACTUATION MECHANISM FOR USE WITH AN ULTRASONIC SURGICAL INSTRUMENT, Ser. No. 11/246,826, filed Oct. 7, 2005, abandoned;

CLAMP MECHANISM FOR USE WITH AN ULTRASONIC SURGICAL INSTRUMENT, Ser. No. 11/246,264, filed Oct. 7, 2005, abandoned;

FEEDBACK MECHANISM FOR USE WITH AN ULTRASONIC SURGICAL INSTRUMENT, Ser. No. 11/246,384, filed Oct. 7, 2005, abandoned;

HANDLE ASSEMBLY HAVING HAND ACTIVATION FOR USE WITH AN ULTRASONIC SURGICAL INSTRUMENT, Ser. No. 11/246,330, filed Oct. 7, 2005, allowed as U.S. Pat. No. 7,846,155;

ULTRASONIC SURGICAL SHEARS AND TISSUE PAD FOR SAME, Ser. No. 11/065,378, filed Feb. 24, 2005, abandoned; and HAND ACTIVATED ULTRASONIC INSTRUMENT, Ser. No. 10/869,351, filed Jun. 16, 2004, application pending.

Further, this application shares a common specification with the following U.S. patent applications: TISSUE PAD FOR ULTRASONIC SURGICAL INSTRUMENT, Ser. No. 11/751,733; ULTRASONIC WAVEGUIDE AND BLADE, Ser. No. 11/751,737; ULTRASONIC BLADE SUPPORT, Ser. No. 11/751,738; and MECHANISM FOR ASSEMBLY OF ULTRASONIC INSTRUMENT, Ser. No. 11/751,741, allowed as U.S. Pat. No. 8,114,104.

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically effected by an end-effector or blade tip at the distal end of the instrument, which transmits ultrasonic energy to tissue brought into contact with the end-effector. Ultrasonic instruments of this nature can be configured for open surgical use, laparoscopic or endoscopic surgical procedures including robotic-assisted procedures.

Ultrasonic surgical instruments have been developed that include a clamp mechanism to press tissue against the blade of the end-effector in order to couple ultrasonic energy to the tissue of a patient. Such an arrangement (sometimes referred to as a clamp coagulator shears or an ultrasonic transector) is disclosed in U.S. Pat. Nos. 5,322,055; 5,873,873 and 6,325,811, all of which are incorporated herein by reference. The surgeon activates the clamp arm to press the clamp pad against the blade by squeezing on the handgrip or handle.

Some current ultrasonic shears devices, however, have the tendency to create tissue tags. Tissue tags are the tissue that remains clamped in the jaw that is not transected after the majority of the tissue in the jaw has been transected and falls away. Tissue tags may result from insufficient end-effector or blade tip proximal loading and/or lower proximal blade activity. Surgeons may mitigate tissue tags either through the addition of vertical tension (i.e. putting tension on the tissue using the blade) or rearward traction on the device in order to move the untransected tissue to a more active portion of the blade to complete the cut.

Some current ultrasonic shears devices utilize tissue pads that close in parallel with the surface of the blade. This presents certain problems in terms of the pressure profile exerted on the tissue. As tissue is compressed between the jaw and the blade, the distal portion of the blade deflects under load more than the proximal portion of the blade. This deflection is created in part by the portion of the blade distal to the most distal node of the device. It is also partly created by the deflection of the waveguide or transmission rod proximal to the most distal node. Additionally, the fact that blade amplitude decreases moving proximal of the tip of the blade makes the situation worse since the amount of energy transferred to the tissue, even if the pressure was constant, is reduced.

Current tissue pad designs utilize PTFE material to contact the tissue and blade. Although these designs have been adequate, they tend to suffer from longevity issues since the pads tend to deteriorate over long surgical procedures. Additionally, newer designs of clamp coagulator shears increase blade amplitude and/or the loading of the pad against the tissue and blade and overwhelm the pad material, resulting in less than required tissue pad life. The pad material limits the amount of force that may be applied against the tissue and blade, which in turn limits the tissue thickness or vessel size that some current clamp coagulator shears may effectively cut and coagulate. Current composite pads may be difficult or expensive to manufacture.

Some current designs of clamp coagulator ultrasonic shears are limited in the length of the active blade available for use by surgeons due to inherent limitations in the effective transfer of mechanical motion along the longitudinal path of the blade from the transducer assembly. Although new blade geometry has mitigated some of these problems, longer active blade lengths, or blades that have more mass (created by larger diameter or larger lengths) have a tendency to shrink the frequency window between resonant and anti-resonant frequencies making it difficult or impossible for ultrasonic generators to lock on to the proper frequency to drive the waveguide, blade and transducer assembly.

Some current designs of clamp coagulator shears utilize elastomer material such as silicone for node supports along the length of the blade. The most distal node support is typically silicone to provide for a seal around the blade. Where higher clamp forces are desired, as is the case with longer active blade lengths, it is desirable to have a rigid distal node support. Many problems, however, are inherent with rigid node supports. Materials such as thermoset polymers that are capable of withstanding the pressure and temperature requirements of an ultrasonic blade node support are often too expensive to be utilized in production. The use of thermoplastics would improve manufacturability from a cost perspective but may not hold up to the pressure and temperature requirements of an ultrasonic blade node support.

Some current designs of clamp coagulator shears utilize a constant force spring mechanism that prevents the application of too much force to the clamp arm and blade. Although the mechanism provides relatively constant force to the system, the spring imparts some slope to the force curve. In applications where the clamp force is low, the slope is not significant. In applications with high clamp forces, however, the difference in force attributable to the slope over the possible range of spring compressions becomes very significant and may exceed the maximum force allowable in the blade, in the tube assemblies or in other components of the system. The high slope could allow the maximum force to be exceeded under abuse modes or through normal manufacturing tolerance variations. If this occurs, the blade may bend, the actuation mechanism may fail or undesirable tissue effects may occur (i.e. fast cutting, but minimal tissue coagulation). This situation is aggravated by the fact that a portion of the jaw (the clamp arm and pad) of the device can meet sufficient resistance to engage the force limiting mechanism when the clamp pad almost contacts the blade (when transecting thin tissue or at the end of the transection or clamping solid objects such as other devices) or when the clamp arm is still open with respect to the blade (when transecting thick tissue).

Some current designs of clamp coagulator shears utilize force-limiting springs to ensure that clamp forces are within a specified range. It is also necessary for the force-limiting spring design to allow the surgeon to "feather" (apply less than the maximum force and slowly increase to the maximum force). In these mechanisms, therefore, the jaw closes until a predetermined force is met and then the additional stroke drives the mechanism into the force limiting range. In some cases, though, the surgeon may, unknowingly, fail to apply the full force of the jaw against the tissue resulting in incomplete tissue cuts or insufficient coagulation. Alternatively, the surgeon may unknowingly open the clamp arm during a transection that results in incomplete tissue cuts or insufficient coagulation.

Some current designs of clamp coagulator shears utilize a foot pedal to energize the surgical instrument. The surgeon operates the foot pedal while simultaneously applying pressure to the handle to press tissue between the jaw and blade to activate a generator that provides energy that is transmitted to the cutting blade for cutting and coagulating tissue. Key drawbacks with this type of instrument activation include the loss of surgeon focus on the surgical field while the surgeon searches for the foot pedal, the foot pedal gets in the way of the surgeon's movement during a procedure and surgeon leg fatigue during long cases.

Some current designs of torque wrenches for ultrasonic surgical instruments utilize a multi-piece torque wrench for use in properly torqueing an instrument to an ultrasonic handpiece. A multi-piece assembly is more costly in that separate pieces have to be molded and then assembled. In addition, the pieces have a tendency to wear rapidly leading to failure of the wrench.

It would be desirable to provide an ultrasonic surgical instrument that overcomes some of the deficiencies of current instruments. The ultrasonic surgical instrument described herein overcomes those deficiencies.

SUMMARY OF THE INVENTION

The present invention meets the above stated needs for an improved tissue pad for an ultrasonic surgical instrument. The tissue pad for use in an ultrasonic clamp coagulator comprises i) a first tissue pad portion, the first tissue pad portion having a distal end a proximal end, a tissue engaging surface and a cavity having an opening coinciding with the tissue engaging surface, and ii) a second tissue pad portion, the second tissue pad portion made from a composition having a greater resistance to heat than the first tissue pad portion, the second tissue pad portion having a tissue engaging surface and sized for placement within the cavity.

A method of mounting the first tissue pad portion onto a clamp arm of an ultrasonic clamp coagulator, comprises the steps of: i) inserting the first tissue pad portion into the clamp arm, the first tissue pad portion being oriented during the insertion so that the cavity is positioned at the proximal portion of the arm, and ii). inserting into the cavity a second tissue pad portion made from a composition having a greater resistance to heat than the first tissue pad portion, the second tissue pad portion having a tissue engaging surface and sized for placement within the cavity.

BRIEF DESCRIPTION OF THE FIGURES

The novel features of the invention are set forth with particularity in the appended claims. The invention itself, however, both as to organization and methods of operation, may best be understood by reference to the following description, taken in conjunction with the accompanying drawings in which:

FIG. 3 is a plan view of one embodiment of the waveguide and blade assembly in accordance with the present invention;

FIG. 3a is a sectional view of one embodiment of the distal end of the blade assembly in accordance with the present invention;

FIG. 3b is a plan view of one embodiment of the waveguide and blade assembly and silicone support rings in accordance with the present invention;

FIG. 4c is a plan and cross sectional view of one embodiment of a clamp arm of the present invention;

FIG. 4d is a perspective elevation view of one embodiment of a tissue pad insert of the present invention;

DETAILED DESCRIPTION OF THE INVENTION

Figure 1:
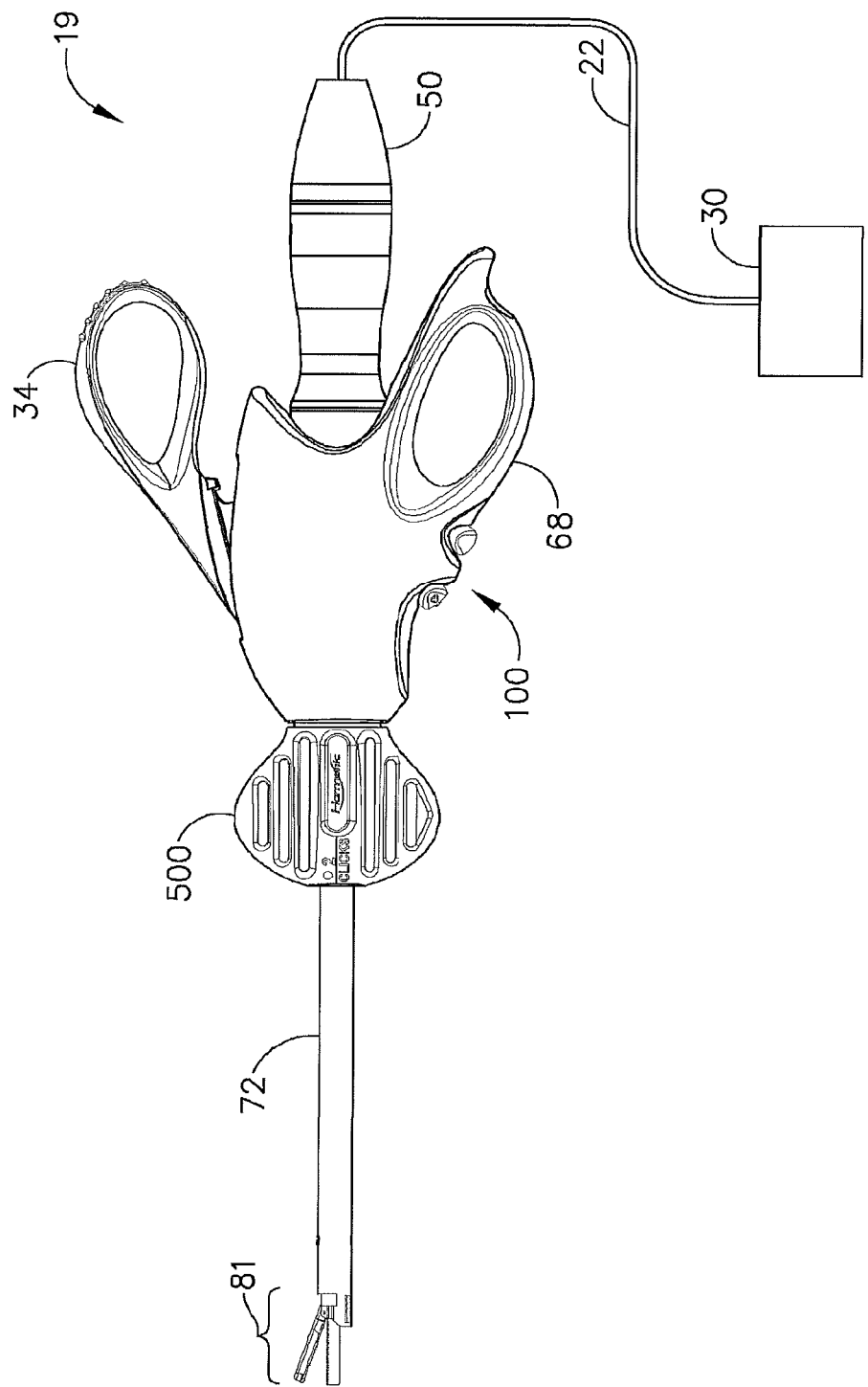
FIG. 1 is a plan view illustrating an embodiment of an ultrasonic surgical instrument in accordance with the present.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Further, unless otherwise indicated, the terms and expressions employed herein have been chosen for the purpose of describing the illustrative embodiments of the present invention for the convenience of the reader and are not for the purpose of limiting the invention.

Further, it is understood that any one or more of the following-described embodiments, expressions of embodiments, examples, etc. can be combined with any one or more of the other following-described embodiments, expressions of embodiments, examples, etc.

The present invention is particularly directed to an improved ultrasonic surgical clamp coagulator apparatus which is configured for effecting tissue cutting, coagulation, and/or clamping during surgical procedures. The present apparatus can be readily configured for use in open surgical procedures, as well as laparoscopic or endoscopic procedures and robot-assisted surgical procedures. Versatile use is facilitated by selective use of ultrasonic energy. When ultrasonic components of the apparatus are inactive, tissue can be readily gripped and manipulated, as desired, without tissue cutting or damage. When the ultrasonic components are activated, the apparatus permits tissue to be gripped for coupling with the ultrasonic energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic blade.

As will become apparent from the following description, the present clamp coagulator apparatus is particularly configured for disposable use by virtue of its straightforward construction. As such, it is contemplated that the apparatus be used in association with an ultrasonic generator unit and transducer of a surgical system, whereby ultrasonic energy from the generator unit provides the desired ultrasonic actuation through the transducer for the present clamp coagulator apparatus. It will be appreciated that a clamp coagulator apparatus embodying the principles of the present invention can be configured for non-disposable or multiple uses, and non-detachably integrated with an associated hand piece (or transducer) unit. However, detachable connection of the present clamp coagulator apparatus with an associated ultrasonic hand piece is presently preferred for single-patient use of the apparatus.

The present invention will be described in combination with an ultrasonic instrument as described herein. Such description is exemplary only, and is not intended to limit the scope and applications of the invention. For example, the invention is useful in combination with a multitude of ultrasonic instruments including those described in, for example, U.S. Pat. Nos. 5,938,633; 5,935,144; 5,944,737; 5,322,055; 5,630,420; and 5,449,370.

Figure 2:
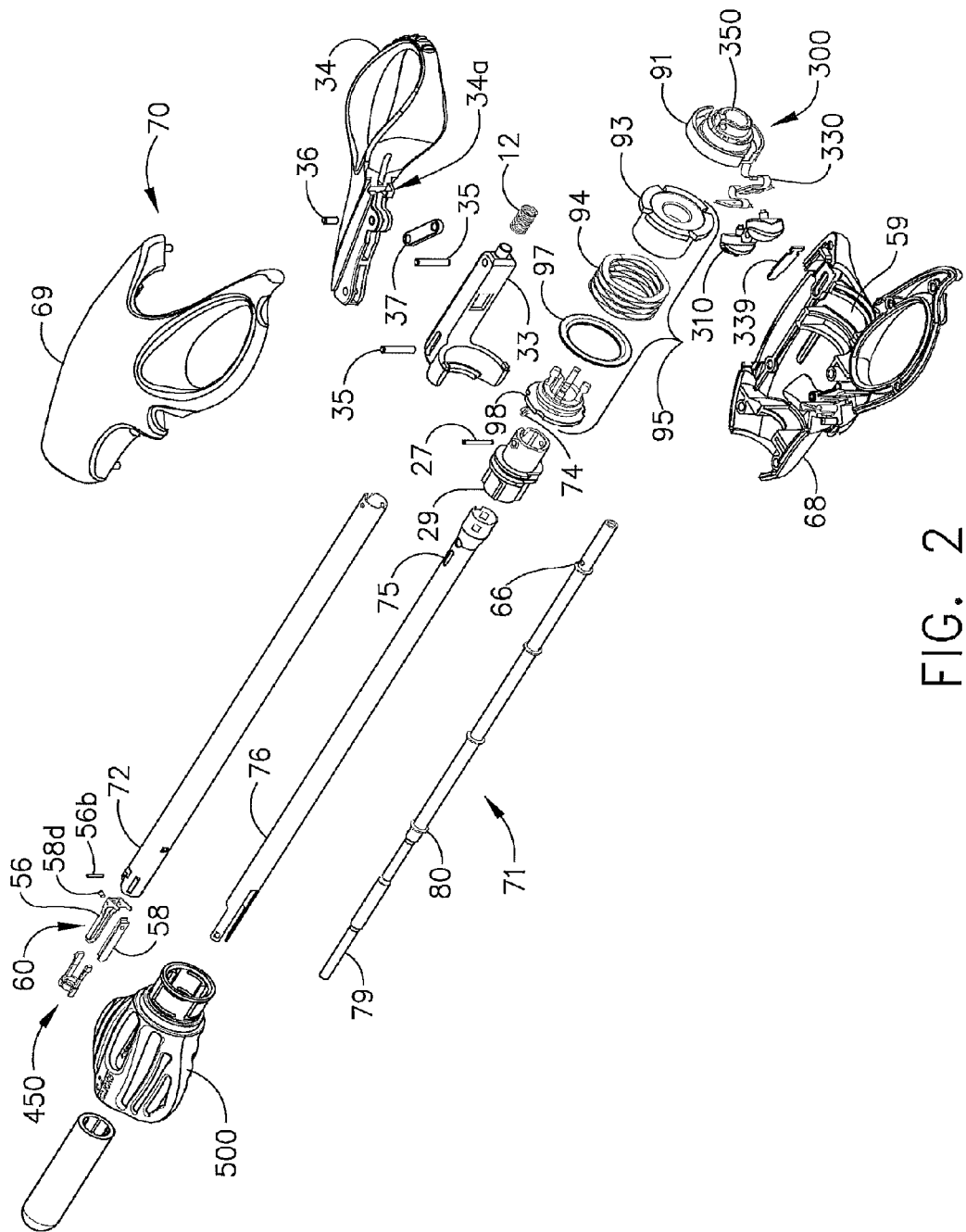
FIG. 2 is a perspective assembly view of an embodiment of an ultrasonic surgical instrument in accordance with the present invention.

With reference to FIGS. 1-3, an embodiment of a surgical system 19, including an ultrasonic surgical instrument 100 in accordance with the present invention is illustrated. The surgical system 19 includes an ultrasonic generator 30 connected to an ultrasonic transducer 50 via cable 22, and an ultrasonic surgical instrument 100. It will be noted that, in some applications, the ultrasonic transducer 50 is referred to as a "hand piece assembly," or simply "hand piece," because the surgical instrument of the surgical system 19 is configured such that a surgeon may grasp and manipulate the ultrasonic transducer 50 during various procedures and operations. A suitable generator is the GEN 300™ sold by Ethicon Endo-Surgery, Inc. of Cincinnati, Ohio.

The ultrasonic surgical instrument 100 includes a multi-piece handle 70 adapted to isolate the operator from the vibrations of the acoustic assembly contained within transducer 50. The handle 70 can be shaped to be held by a user in a conventional manner, but it is contemplated that the present ultrasonic surgical instrument 100 principally be grasped and manipulated by a scissor-like arrangement provided by a handle assembly of the instrument, as will be described. While single-piece handle 70 is illustrated, the handle 70 may comprise a single or unitary component. The proximal end of the ultrasonic surgical instrument 100 receives and is fitted to the distal end of the ultrasonic transducer 50 by insertion of the transducer into the handle 70. The ultrasonic surgical instrument 100 may be attached to and removed from the ultrasonic transducer 50 as a unit.

Referring specifically now to FIG. 2, the ultrasonic surgical instrument 100 may include a handle assembly 70, comprising mating housing portions 68 and 69, together forming handle 70 and a transmission assembly 71. The ultrasonic surgical instrument 100 has application in both open and endoscopic surgical procedures. The construction can be dimensioned such that transmission assembly 71 has an outside diameter of approximately 8.5 mm. The elongated transmission assembly 71 of the ultrasonic surgical instrument 100 extends orthogonally from the instrument handle 70. The handle 70 may be constructed from a durable plastic, such as polycarbonate or a liquid crystal polymer. It is also contemplated that the handle 70 may alternatively be made from a variety of materials including other plastics, ceramics or metals.

The transmission assembly 71 may include an outer tubular member or outer sheath 72, an inner tubular actuating member 76, a waveguide 80 and end-effector 81 (blade 79, clamp arm 56, pin 56b and one or more clamp pads 58). As will be described, the outer sheath 72, the actuating member 76, and the waveguide or transmission rod 80 may be joined together for rotation as a unit (together with ultrasonic transducer 50) relative to handle 70. The waveguide 80, which is adapted to transmit ultrasonic energy from transducer 50 to blade 79 may be flexible, semi-flexible or rigid.

The ultrasonic waveguide 80 may further include at least one radial hole or aperture 66 extending there through, substantially perpendicular to the longitudinal axis of the waveguide 80. The aperture 66, which may be positioned at a node, is configured to receive an insulated connector pin 27, which connects the waveguide 80, to the tubular actuating member 76, and the tubular outer sheath 72, as well the outer tube retainer 29. A rotation knob 28 (not shown) may be added to or may replace retainer 29 to facilitate rotation of the blade assembly 80, including the end effector 81 relative to instrument handle 70, as is known and understood in the art.

The blade 79 may be integral with the waveguide 80 and formed as a single unit. In an alternate expression of the current embodiment, a threaded connection, a welded joint, or other coupling mechanisms may connect blade 79 to waveguide 80. The distal end of the blade 79 is disposed near an anti-node in order to tune the acoustic assembly to a preferred resonant frequency $f_o$ when the acoustic assembly is not loaded by tissue. When ultrasonic transducer 50 is energized, the distal end of blade 79 is configured to move longitudinally in the range of, for example, approximately 10 to 500 microns peak-to-peak, and preferably in the range of about 20 to about 200 microns at a predetermined vibrational frequency $f_o$ of, for example, 55,500 Hz.

Referring now to FIG. 3, the waveguide 80 may also be configured to amplify the mechanical vibrations transmitted through the waveguide 80 to the blade 79 as is well known in the art and more fully described in ULTRASONIC SURGICAL BLADE AND INSTRUMENT HAVING A GAIN STEP, Ser. No. 10/701,558, filed Nov. 5, 2003, now U.S. Pat. No. 7,163,548 B2, which is incorporated herein by reference. In one embodiment of the present invention, the waveguide 80 may further have features to control the gain of the longitudinal vibration along the waveguide 80 and features to tune the waveguide 80 to the resonant frequency of the system. In particular, waveguide 80 may have any suitable cross-sectional dimension. For example, the waveguide 80 may have a substantially uniform cross-section or the waveguide 80 may be tapered at various sections or may be tapered along its entire length as is described in more detail herein.

In one embodiment of the present invention, the waveguide 80 includes a hollow bore 101 located between the most distal vibration node and the distal tip of the blade 79a. This hollow bore 101 in the instant embodiment, facilitates longer active blade length by stretching or expanding wavelength as is known and understood in the art. This longer active blade length may require larger diameter blades 79 to facilitate the bore. To ensure proper performance of the blade 79 and to achieve desired cutting and coagulation action of the blade, a larger wave amplitude may be used. Increasing active blade length and wave amplitude may create difficulties for the system to achieve resonance. For instance, a system tuned to resonate at 55,500 Hz, with the hollow bore blade, may achieve anti-resonance at 55,550 Hz. This narrow frequency window may make it difficult or impossible for the generator 30 (see FIG. 1) to continuously drive the waveguide 80 and blade 79 system at its resonant frequency.

To enable larger wave amplitude and longer active blade lengths and still provide sufficient frequency margin or window, a waveguide 80 is provided with a series of gain steps in the waveguide 80. The gain of a gain step less than unity results from an increase in mass of the ultrasonic waveguide at a node, and the gain of a gain step greater than unity results from a decrease in mass of the waveguide at a node. A gain feature is any one of geometric constructions of the waveguide or blade that either increases or decreases the mass of the waveguide or blade at a node and include: a discrete change in outer diameter or perimeter, a taper, a longitudinal hole, a transverse hole, a void, a surface flat, a surface slot, and a change in material. The term hole includes a through hole and a non-through hole. Other gain features are left to the artisan.

In one embodiment of the present invention, a gain step 102, located at the second most distal vibration node (see FIG. 3), is provided in the waveguide 80. Gain step 102 decreases the cross sectional area of the blade facilitating greater wave amplitude in the decreased diameter (see FIG. 3c), as is known and understood in the art. To facilitate the longer active blade length and to maintain a desired blade diameter, a step up 103 is provided at or near an antinode, which increases the cross sectional area of waveguide 80 without affecting the gain. In one embodiment, the step up 103 is located at the second most distal vibration antinode in relation to the distal blade tip 79a. A second step down or gain step 104 is provided adjacent to the blade 79. The second gain step 104 results in a second amplitude increase. In one embodiment, the second gain step 104 is located at the first most distal vibration node in relation to the blade tip 79a.

As is known and understood in the art, in an ultrasonic blade system, a generator produces a current to drive a transducer located within handpiece 50. This transducer imparts mechanical energy at a specific frequency to a waveguide and to a blade attached thereto. The generator continues to impart electrical energy to convert to mechanical energy as it varies the frequency in an effort to find and drive the system at its resonant frequency. Equating the transducer and waveguide as an equivalent electrical model, as the frequency of cycling is increased, starting at a non-resonant condition below the desired resonant frequency, the system's oscillations first approach a frequency at which impedance is minimum (maximum admittance). This minimum impedance frequency approximates the series resonance frequency, the frequency at which impedance in an electrical circuit describing the element is zero (assuming resistance caused by mechanical losses is ignored). The minimum impedance frequency also is the resonant frequency of the waveguide and blade assembly, which by design is nominally the same resonant frequency of the transducer. The composition of the transducer material and the shape and volume of the waveguide and blade assembly determine the resonance frequency. As the cycling frequency is further increased, impedance increases to a maximum (minimum admittance). The maximum impedance frequency, approximates the parallel resonance frequency, the frequency at which parallel resistance in the equivalent electrical circuit is infinite (assuming resistance caused by mechanical losses is ignored). The maximum impedance frequency also is the anti-resonance frequency. The larger the difference between resonant and anti-resonant frequencies (that is, the frequency window or phase margin), the easier it is for a generator to establish and maintain resonance in the waveguide and blade assembly as frequency tolerances are relaxed.

Figure 3C:
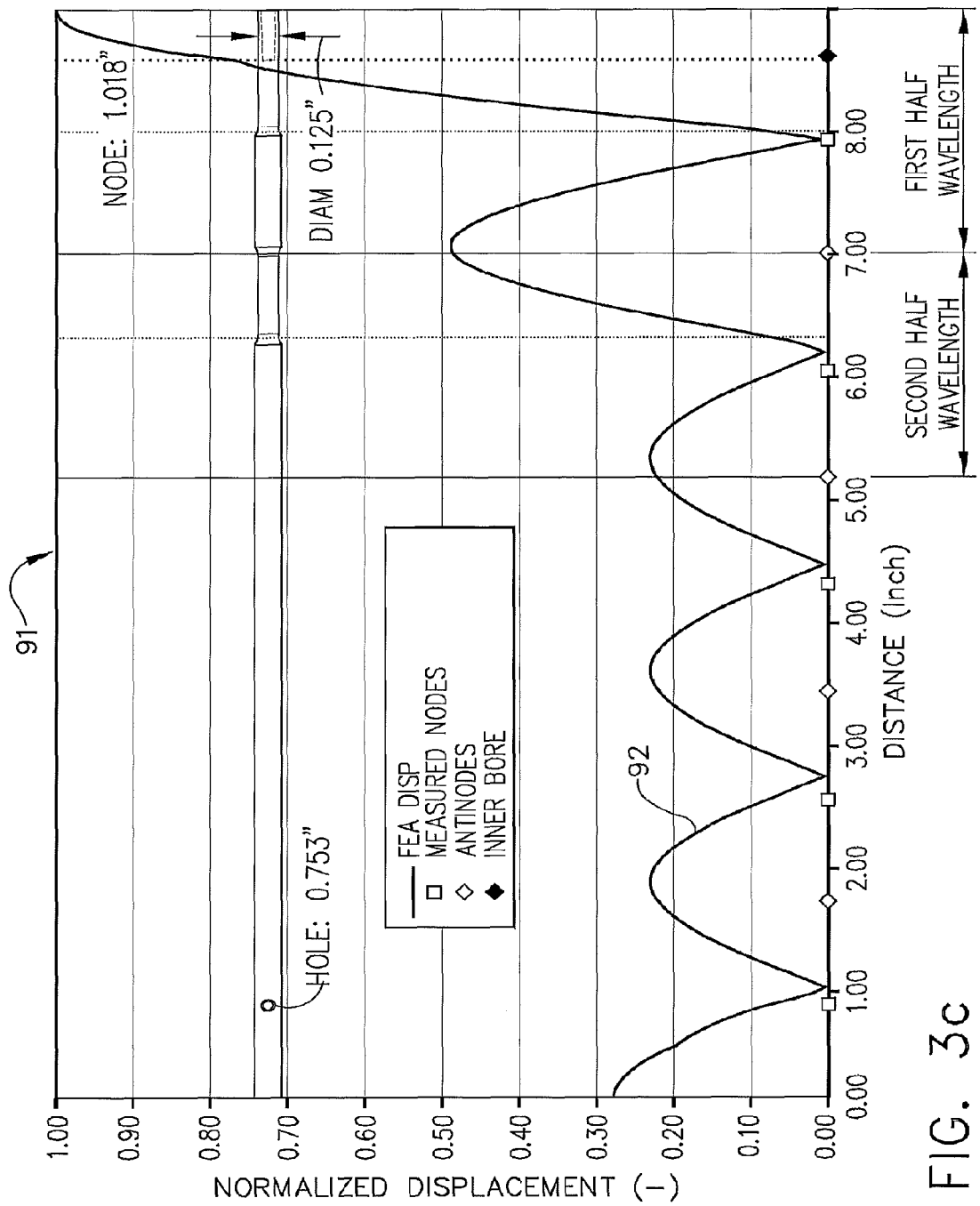
FIG. 3c is a graph depicting waveform along the length of the waveguide and blade of one embodiment of the present invention.

In the present invention, the gain step described above may cause a significant acoustic impedance mismatch, causing some of the mechanical energy transmitted along the waveguide to be reflected. As is seen in FIGS. 3 and 3c, a gain in wave amplitude is caused by a thinner cross section in the waveguide 80 adjacent gain step 102. At gain step 102, the change in thickness results in a lowering of the anti-resonant frequency after the step 102. This results in a narrower frequency window or steeper trough between resonance and anti-resonance. A step up 103 results in an increase in waveguide cross-section or thickness that in part addresses manufacturing requirements.

Applicants have determined that locating the gain steps in the distal portion of the waveguide results in a greater phase margin or wider trough between resonant and anti-resonant frequencies. What is meant as the "distal portion" is the distal half of the waveguide. By delaying waveguide narrowing to the distal end of the waveguide, more mechanical energy is stored along the waveguide and any negative effects due to reflection at the gain steps are mitigated. It is appreciated that the gain step or combination step up/down/up may be located anywhere along the waveguide. For ideal system performance, however, the gain step(s) should be located in the distal half of the blade, preferably at the two most distal nodes in relation to the handpiece, or the two most proximal nodes in relation to the blade tip. Surprisingly, the Applicants found that the phase margin increased by almost 100% by relocating the gain steps to the distal portion of the waveguide. In early experiments of a waveguide having two gain steps, one at the proximal end and one at the distal end, the phase margin measured 30 to 40 Hz. In experiments of a waveguide having two gain steps, both located at the distal portion, the phase margin measured between 50 and 80 Hz. In experiments of a waveguide having two gain steps, one at each of the two most distal nodes, the phase margin measured between 75 and 80 Hz.

In another embodiment (not shown), a single gain step is located at either the first or second most distal node in relation to the tip of the blade 79a. A single gain step may obviate the need for a step up and step down on the blade. To accommodate the hollow tip blade, the waveguide 80 must be of sufficient cross section to transmit a wave from the handpiece to the first gain step 102 and the difference in diameters between the waveguide and the blade must be sufficient to result in the wave amplitude gain from a step down, step up and step down combination. The diameter difference must be large enough to achieve correct blade longitudinal excursion while providing a sufficient frequency window for the system to lock on to resonance.

Referring again to FIG. 3, a waveguide 80 and blade 79 combination is shown. In one embodiment, the overall length of the combination is 8.854 inches. The first gain step 102 is located 6.139 inches from proximal end 90. The step up 103 is located 6.922 inches from end 90. The second gain step 104 is located 7.912 inches from end 90. The bore 101 is 0.384 inches measured from blade tip 79a.

Referring now to FIG. 3c, graph 91 displays wave amplitude vs. blade distance and geometry. The y-axis represents wave amplitude given as a percentage of maximum displacement. The x-axis represents blade length. The wave 92 represents the response or gain along the length due to the varying cross sections in waveguide 80 and blade 79 discussed in reference to FIG. 3. The points at which the wave 92 crosses the x-axis are referred to as nodes or vibration nodes. The points at which wave 92 reaches maximum amplitude are referred to as antinodes. It can be seen that the first gain in wave amplitude 92 corresponds with gain step 102 and the second gain in wave amplitude 92 occurs at second gain step 104.

Referring to FIG. 3b, waveguide 80 may have a plurality of stabilizing silicone rings 80a or compliant supports to prevent the waveguide 80 from making contact with the inner tube 76 during activation. The silicone rings 80a are ideally located at nodes on the waveguide 80 as is known and understood in the art. Rings 80a are preferably over molded on waveguide 80 to ensure accurate location. A seal may be provided at the distalmost node, nearest the end-effector 81, to abate passage of tissue, blood, and other material in the region between the waveguide 80 and actuating member 76. A silicone ring may not be sufficient at the most distal node of the waveguide 80 in the instant embodiment of the present invention. As discussed above, the waveguide 80 is provided with amplitude gain steps 102 and 104 that amplify the wave transmitted to the blade 79. The greatest deflection of the blade occurs at the blade tip 79a. To facilitate tissue cutting in the proximal portion of the blade 79, a node support more rigid than silicon (a "rigid" support) is preferable to promote wave transmission to the blade to prevent wave absorption or losses and further provide more accurate dimensional stability of the blade deflection relative to the clamp arm 56. A rigid support may be useful in promoting higher clamp forces in the proximal portion of blade 79 since a rigid support will not compress or yield at higher clamp forces as would silicone or like materials.

Figure 3D:
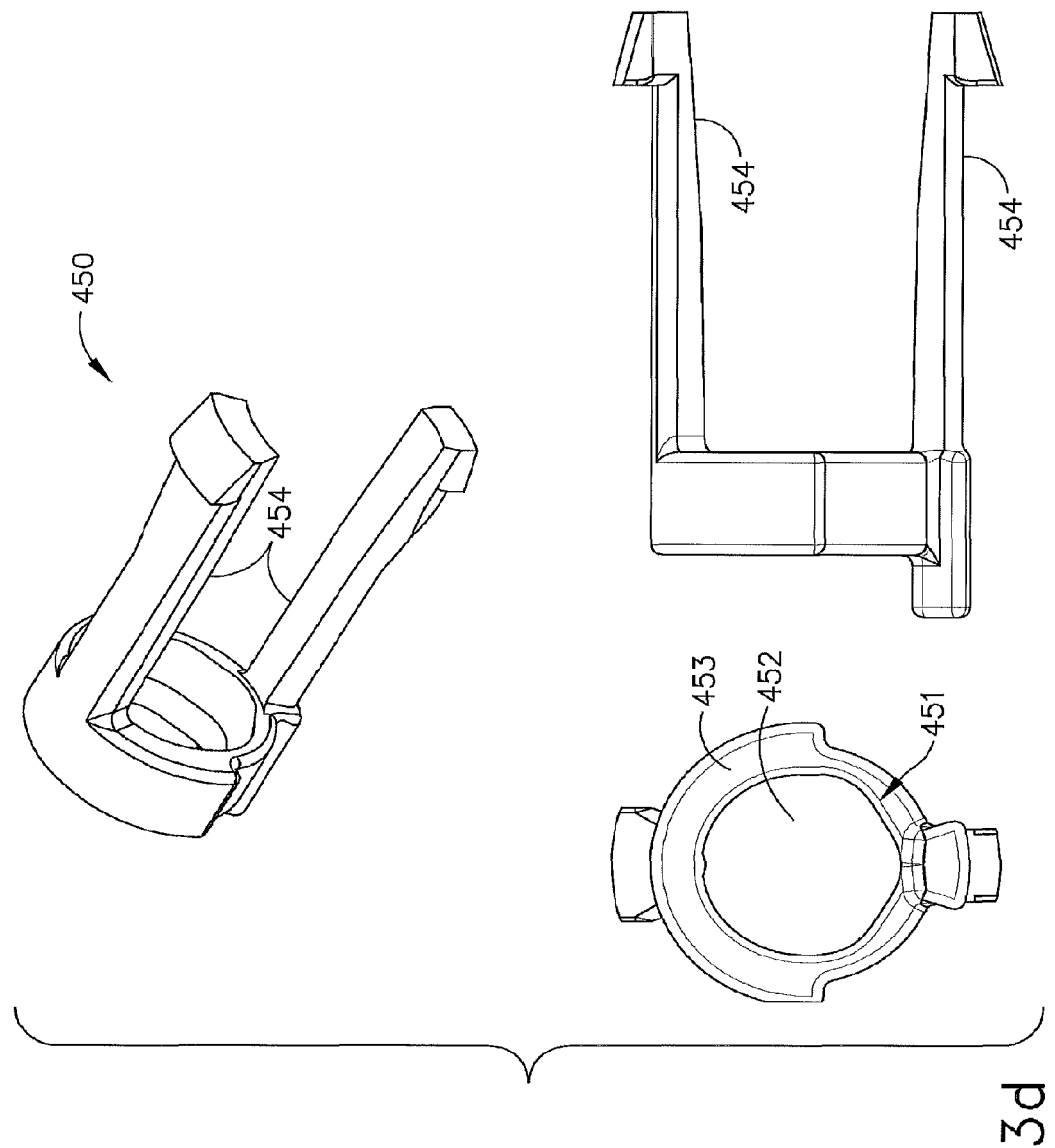
FIG. 3d is a perspective, side view and cross sectional view of one embodiment of a distal blade node support.

Referring back to FIG. 2 and now FIG. 3d, a blade support 450 is shown. In a first expression of a first embodiment, support 450 is comprised of two pieces. A sleeve 451 preferably composed of a thermoset polymer is disposed around annular opening 452. The sleeve may be manufactured from bar stock resin such as VESPEL 211. The sleeve 451 is then insert molded or pressed into a less expensive thermoplastic resin collar 453. The collar 453 is preferably composed of a filled thermoplastic resin with high thermal-conductivity, such as a filled PEEK. In this two-piece configuration, the support 450 is able to withstand the temperature and pressures associated with operation of the ultrasonic blade 79 and waveguide 80. In operation, when the blade is activated, heat built up in the blade is transferred through the thermoset polymer insert 451 to the collar 453. The collar 453 transfers the heat to fins 454. Fins or supports 454 support the collar 453 in the outer tube or sheath 72 and also transfer heat away from the collar 453 and insert 451 into the void between the blade 79 and the actuating member 76. In a second expression of a first embodiment, blade support 450 is comprised of a thermoplastic resin, such as PEEK, of unitary construction. In a third expression of a first embodiment, blade support 450 is comprised of a thermoset polymer of unitary construction or a high temperature injection molded polyamide or compression molded materials of unitary construction. Other materials, such as ceramics and metals are also contemplated for the blade support 450 as is well known to the artisan.

Ultrasonic transducer 50, and an ultrasonic waveguide 80 together provide an acoustic assembly of the present surgical system 19, with the acoustic assembly providing ultrasonic energy for surgical procedures when powered by generator 30. The acoustic assembly of surgical instrument 100 generally includes a first acoustic portion and a second acoustic portion. In the present embodiment, the first acoustic portion comprises the ultrasonically active portions of ultrasonic transducer 50, and the second acoustic portion comprises the ultrasonically active portions of transmission assembly 71. Further, in the present embodiment, the distal end of the first acoustic portion is operatively coupled to the proximal end of the second acoustic portion by, for example, a threaded connection.

Figure 9:
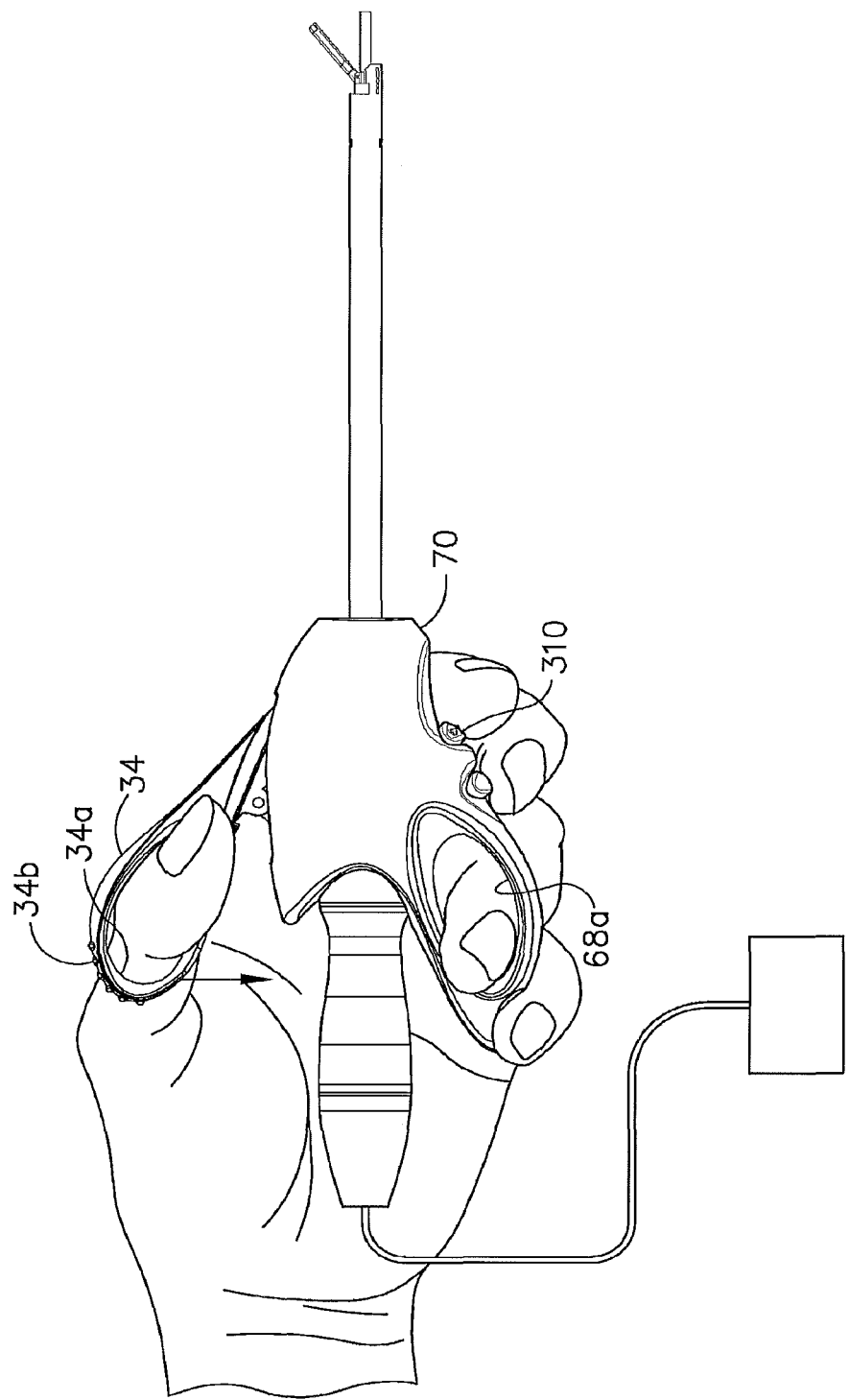
FIG. 9 is a plan view of an ultrasonic surgical instrument in accordance with the present invention with the a first finger accessing a first activation button gripped by a left-handed surgeon.
Figure 10:
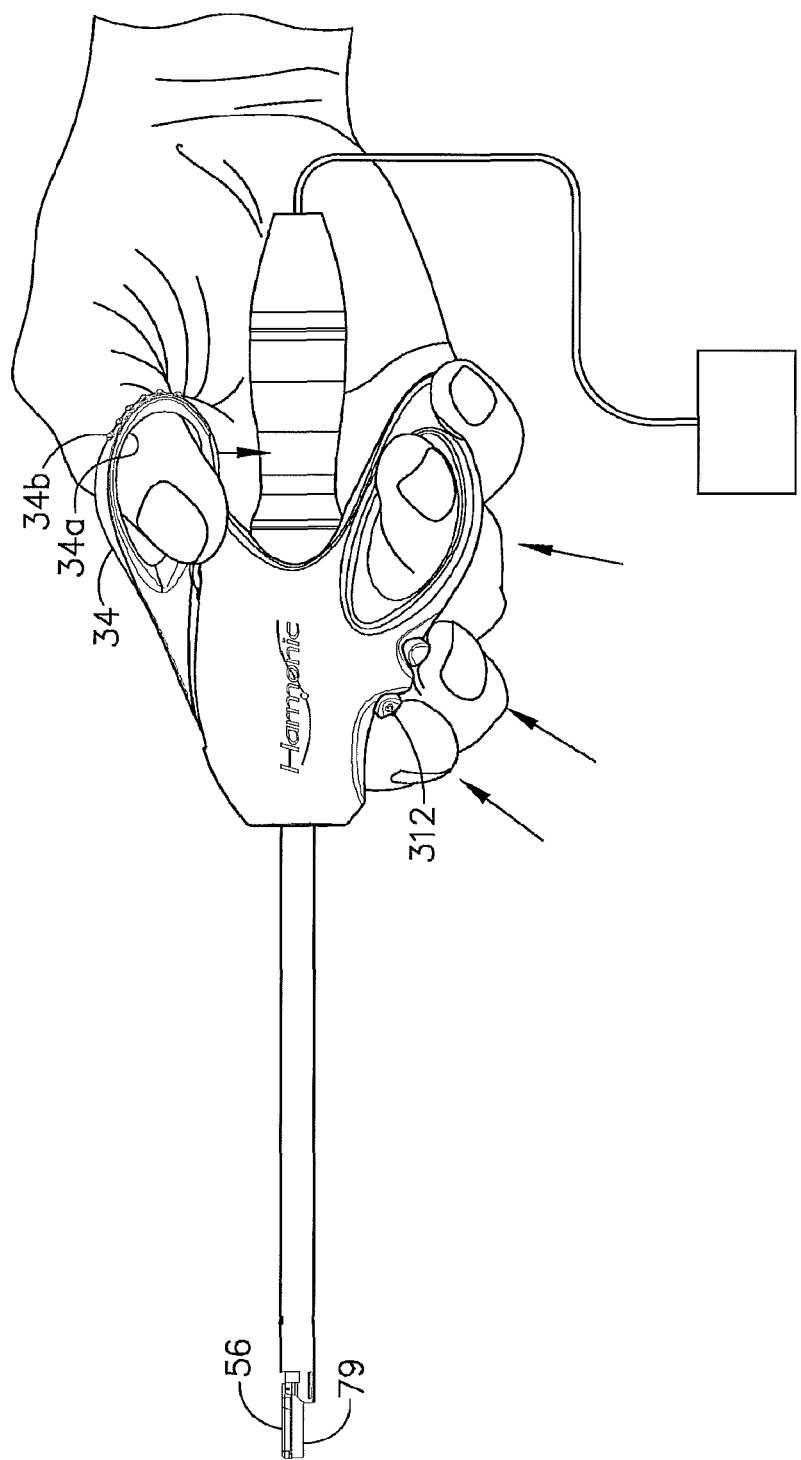
FIG. 10 is a plan view of an ultrasonic surgical instrument in accordance with the present invention with the a first finger accessing a first activation button gripped by a right-handed surgeon.

With particular reference to FIGS. 2, 9 and 10, reciprocal movement of actuating member 76 drives the clamp member 60 open and closed. A force-limiting mechanism 95 is operatively connected to actuating member 76 and comprises a tube collar 98 that secures distal washer 97, wave spring 94, onto threaded collar cap 93. Outer tube retainer 29 engages with openings 75 in the proximal portion of tubular actuating member 76 via insulated pin 27. A shoulder 74 on the tube collar 78 receives drive yoke 33 for engagement with the inside surface of outer sheath 72.

The force limiting mechanism 95 provides a portion of the clamp drive mechanism of the instrument 100, which affects pivotal movement of the clamp member 60 by reciprocation of actuating member 76. The clamp drive mechanism further includes a drive yoke 33 which is operatively connected with an operating trigger handle 34 of the instrument, with the operating trigger handle 34 thus interconnected with the reciprocable actuating member 76 via drive yoke 33 and force limiting mechanism 91. Trigger handle 34 is connected to drive yoke 33 and link 37 via pins 35 and 36. Spring 12 is located between drive yoke 33 and handle assembly 68 and 69 biasing reciprocable actuating member 76 to the open position.

Movement of trigger handle 34 toward handgrip 70 translates actuating member 76 proximally, thereby pivoting clamp member 60 toward blade 79. The scissor-like action provided by trigger handle 34 and cooperating handgrip 70 facilitates convenient and efficient manipulation and positioning of the instrument, and operation of the clamping mechanism at the distal portion of the instrument whereby tissue is efficiently urged against the blade 79. Movement of trigger handle 34 away from handgrip 68 translates actuating member 76 distally, thereby pivoting clamp member 60 away from blade 79.

Figure 4A:
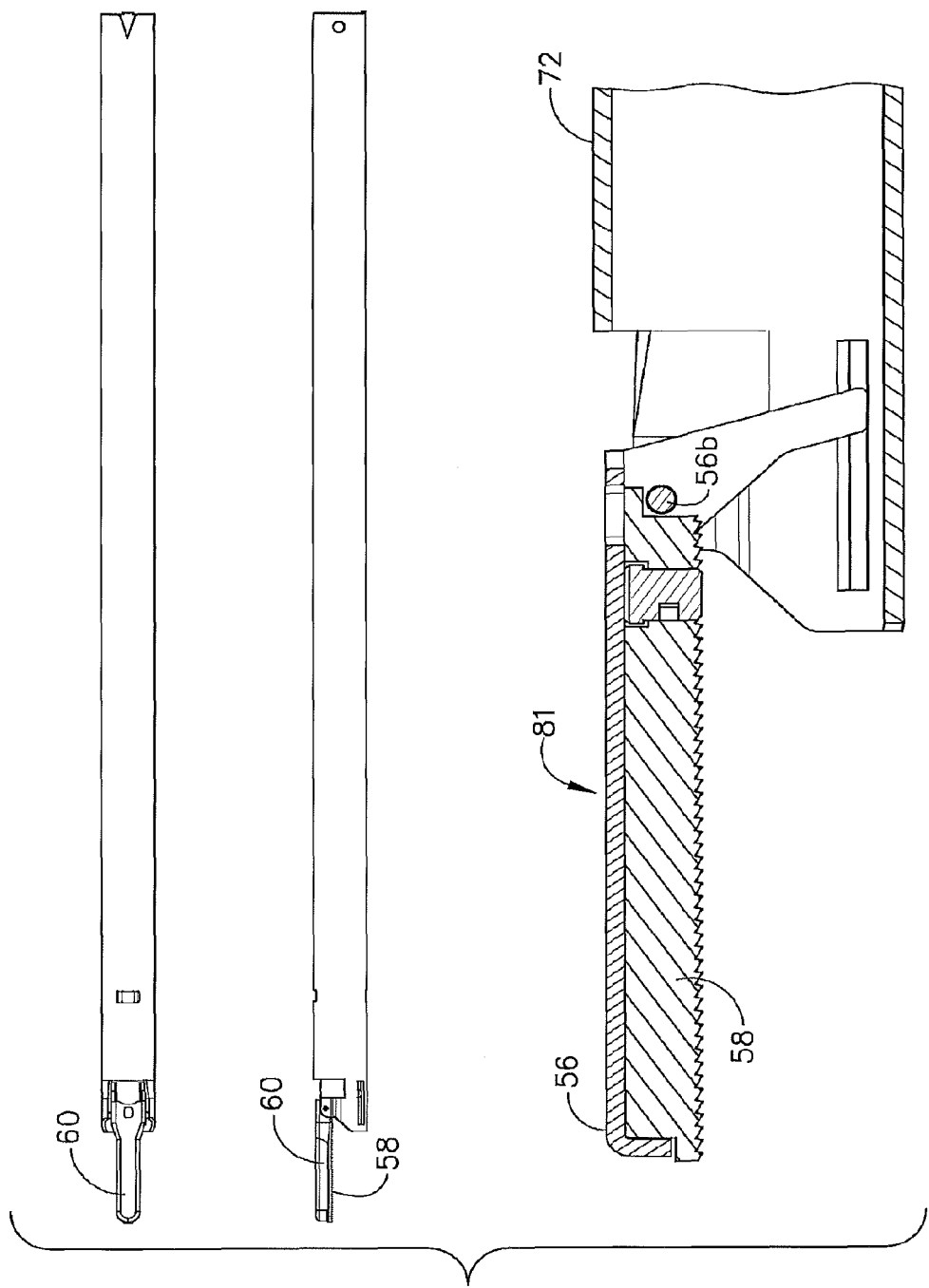
FIG. 4a depicts plan, top and cross sectional views of outer sheath and clamp arm assembly of one embodiment of the present invention.

With particular reference to FIG. 4a, therein is illustrated one embodiment of clamp member 60 for use with the present ultrasonic surgical instrument 100 and which is configured for cooperative action with blade 79 (not shown). The clamp member 60 in combination with blade 79 is commonly referred to as the end effector 81, and the clamp member 60 is also commonly referred to as the jaw. The clamp member 60 includes a pivotally movable clamp arm 56, which is connected to the distal end of outer sheath 72 and actuation member 76 (not shown), in combination with a tissue-engaging pad or clamp pad 58. In one expression of the embodiment, clamp pad 58 is formed from TEFLON® trademark name of E. I. Du Pont de Nemours and Company, a low coefficient of friction polymer material, or any other suitable low-friction material. Clamp pad 58 mounts on the clamp arm 56 for cooperation with blade 79, with pivotal movement of the clamp arm 56 positioning the clamp pad in substantially parallel relationship to, and in contact with, blade 79, thereby defining a tissue treatment region. By this construction, tissue is grasped between clamp pad 58 and blade 79. As illustrated, clamp pad 58 may be provided with non-smooth surface, such as a saw tooth-like configuration to enhance the gripping of tissue in cooperation with the blade 79. The saw tooth-like configuration, or teeth, provide traction against the movement of the blade. The teeth also provide counter traction to the blade and clamping movement. As would be appreciated by one skilled in the art, the saw tooth-like configuration is just one example of many tissue-engaging surfaces to prevent movement of the tissue relative to the movement of the blade 79. Other illustrative examples include bumps, criss-cross patterns, tread patterns, a bead or sand blasted surface, etc.

Tissue pads having composite construction, while having benefits and advantages over TEFLON pads, have cost and manufacturing disadvantages. Composite tissue pads are typically compression molded into a flat coupon. Such compression molding can be time consuming and expensive. Once the flat coupon is produced, it must be machined to produce a tissue pad suitable for use with a clamping ultrasonic device adding further time and expense to the manufacturing process.

With particular reference to FIGS. 4a and b, a first expression of the current embodiment includes a clamp pad 58 having a proximal portion 58b and a distal portion 58a that include a saw tooth like configuration. Clamp pad 58 may be a single component, which has an annular opening 58c. Annular opening 58c is configured to receive pad insert 58d. The advantage of two separate components 58 and 58d is that the pad and the insert may be constructed from different materials. For example, having a two-piece tissue pad allows the use of a very lubricious material at the distal end that is not particularly wear resistant to high temperatures compared to a very high temperature material at the proximal end that is not particularly lubricious because the proximal end is an area of lower amplitude. Such a configuration matches the tissue pad materials to the amplitude of the blade 79. Applicants found, in one experiment, that a 15% graphite-filled, 30% PTFE-filled polyimide tissue pad showed substantially the same or better wear with a 4.5 pound clamping force as a 100% polytetrafluoroethylene (PTFE) tissue pad showed with a 1.5 pound clamping force. The advantage of a 15% graphite-filled, 30% PTFE-filled polyimide tissue pad is increased heat resistance, which improves the overall wear resistance of the tissue pad. This polyimide-composite clamp pad has a useful heat resistance up about 800° F. to about 1200° F., as compared to a useful heat resistance up to about 660° F. of a PTFE clamp pad. Alternatively, Other materials are also useful for a portion of the tissue pad (that is element 58d), such as ceramics, metals, glasses and graphite.

In an alternate expression of the current embodiment, clamp pad 58 includes a proximal portion 58b that is smoother than distal portion 58a (not shown) where distal portion 58a includes a saw tooth like configuration. Proximal portion 58b may be devoid of saw-tooth-like teeth or other tissue engaging surfaces contemplated. Utilizing a smooth proximal portion 58b on clamp pad 58 allows tissue in the proximal region to move distally, following the vibratory motion of the blade, to the more active region of the blade 79 to prevent tissue tagging. This concept takes advantage of the inherent motion profile of blade 79. Due to sinusoidal motion, the greatest displacement or amplitude of motion is located at the most distal portion of blade 79, while the proximal portion of the tissue treatment region is on the order of 50% of the distal tip amplitude. During operation, the tissue in the proximal region of end effector (area of portion 58b) will desiccate and thin, and the distal portion of end effector 81 will transect tissue in that distal region, thereby allowing the desiccated and thin tissue within the proximal region to slide distally into the more active region of end effector 81 to complete the tissue transaction.

In another expression of the current embodiment of the present invention, clamp pad 58a is formed from TEFLON® or any other suitable low-friction material. Pad insert 58d is formed from a composite material, such as a polyimide.

In one expression of one embodiment of the invention, a pad insert 58d is formed from a cylinder of composite material. Referring to FIG. 4c, a pad insert having a varying cross section is depicted. Pad 58d may be a cylinder that is sized to press fit within annular opening 58c. Alternatively, pad insert 58d maybe provided with cutout 58d'. The cutout 58d' is matched to a lip in annular opening in 58c in pad 58. This lip-cutout arrangement facilitates easy insertion of the pad insert 58d into the pad 58 and further promotes mechanical holding action of the pad insert 58d in the pad 58. This mechanical holding action may obviate the need for welding, gluing and the like. In other embodiments, the pad insert 58*d* may be cylindrical with varying steps in the bore to facilitate holding, may be of cylindrical cross section with increasing or decreasing diameter, or may be square, or rectangular and may be provided with barbs on the surface to facilitate holding in the clamp pad 58. Other embodiments may use glue or welding to hold the pad insert 58*d* in place. In other embodiments, the clamp pad 58 may have multiple pad inserts located anywhere along the length of the pad 58.

Several benefits and advantages obtain from one or more of the expressions of the invention. Having a tissue pad with a base material and at-least-one pad insert material allows the base material and the at-least-one pad insert material to be chosen with a different hardness, stiffness, lubricity, dynamic coefficient of friction, heat transfer coefficient, abradability, heat deflection temperature, glass transition temperature and/or melt temperature to improve the wearability of the tissue pad, which is important when high clamping forces are employed because tissue pads wear faster at higher clamping forces than at lower clamping forces. Further benefits and expressions of this embodiment are disclosed in U.S. patent application Ser. No. 11/065,378, filed on Feb. 24, 2005 and commonly assigned to the assignee of the present application.

Referring to FIG. 4*c*, one expression of clamp arm 56 is shown. In this configuration, the clamp arm is stamped from a single piece of material. This stamping process yields a cross section 56*a* and flanges 56*a*' tapered inward to form a channel and adapted to receive a correspondingly shaped wedge or flange 58*e* on clamp pad 58. This single piece stamping process has the advantage of rapid and inexpensive clamp arm 56 manufacture. Additionally, clamp arm 56 omits a pad stop that is found in traditional ultrasonic clamp arms and instead relies on weld pin 56*b* (see FIG. 4*a*) to hold the clamp pad 58 in place further reducing manufacturing cost.

Although a single clamp arm is depicted, clamp arm 56 may comprise a distal T-shaped slot for accepting a T-shaped flange of distal clamp pad and a proximal wedged-shaped or dove tailed-shaped slot for accepting a wedge-shaped flange of a proximal clamp pad as is known and understood in the art. As would be appreciated by those skilled in the art, flanges and corresponding slots have alternate shapes and sizes to secure the clamp pads to the clamp arm. The illustrated flange configurations shown are exemplary only and accommodate the particular clamp pad material of one embodiment, but the particular size and shape of the flange may vary, including, but not limited to, flanges of the same size and shape. For unitary tissue pads, the flange may be of one configuration. Further, other methods of mechanically attaching the clamp pads to the clamp arm, such as rivets, glue, press fit or any other fastening means well know to the artisan are contemplated.

A first expression of a method for replacing clamp pads 58 would include one or more of the steps of: a) removing weld pin 56*b*; b) removing clamp arm 56 from outer sheath 72; c) removing clamp pad 58 from the clamp arm 56; c) removing a pad insert 58*d* from the clamp pad 58; d) inserting a clamp pad into a clamp arm 56; and e) engaging clamp arm 56 with outer sheath 72 via weld pin 56*b*. In this removal and replacement process, the new clamp pad 58 inserted in step "d" may be of unitary TEFLON construction, may be of composite construction, may be multiple pieces of TEFLON or composite material or may contain a pad insert or any combination thereof. Pad insert may be a new pad insert or may be the pad insert from the "used" clamp pad.

Figure 4B:
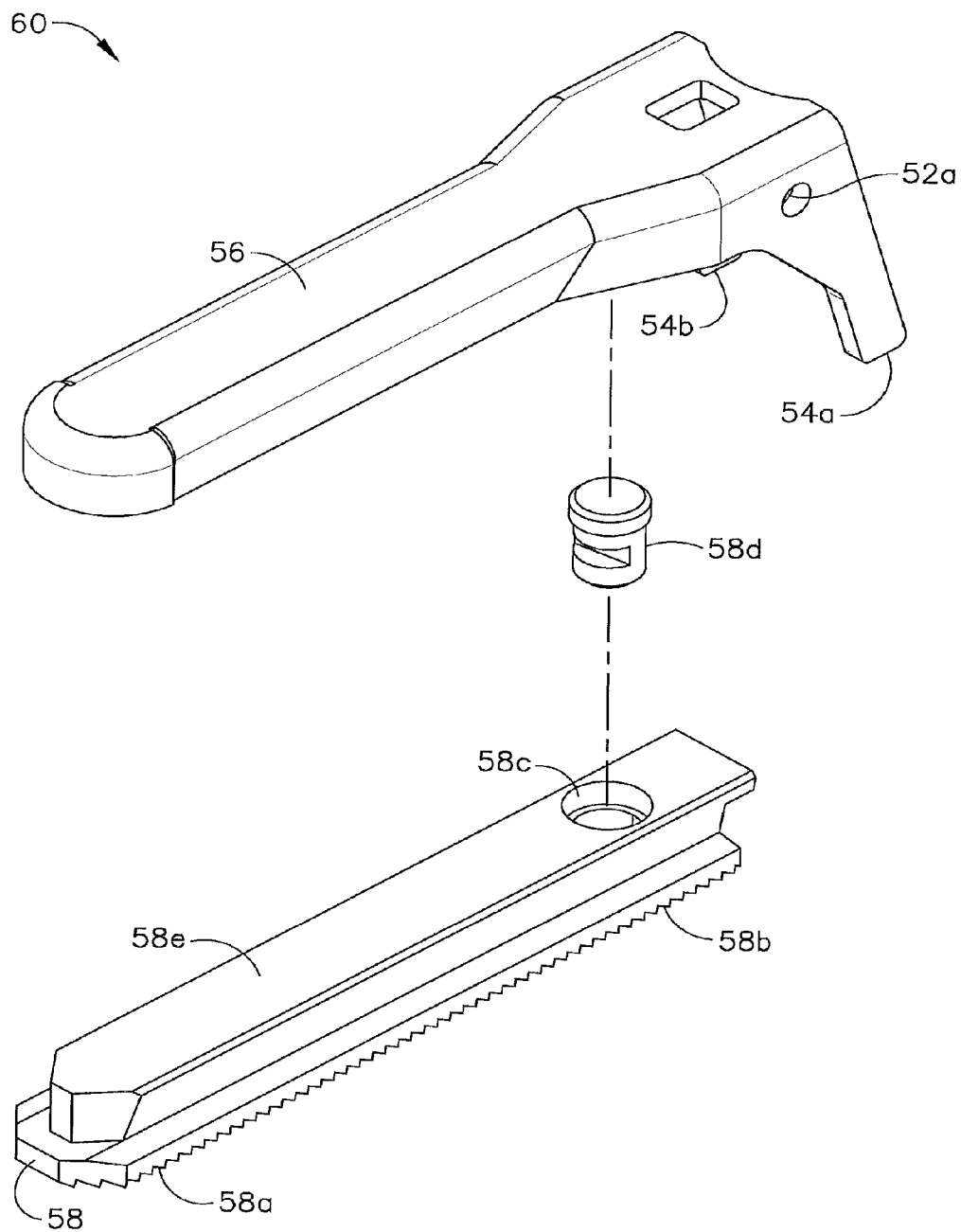
FIG. 4b is a perspective assembly view of one embodiment of a clamp arm and clamp pad assembly of the present invention.
Figure 5:
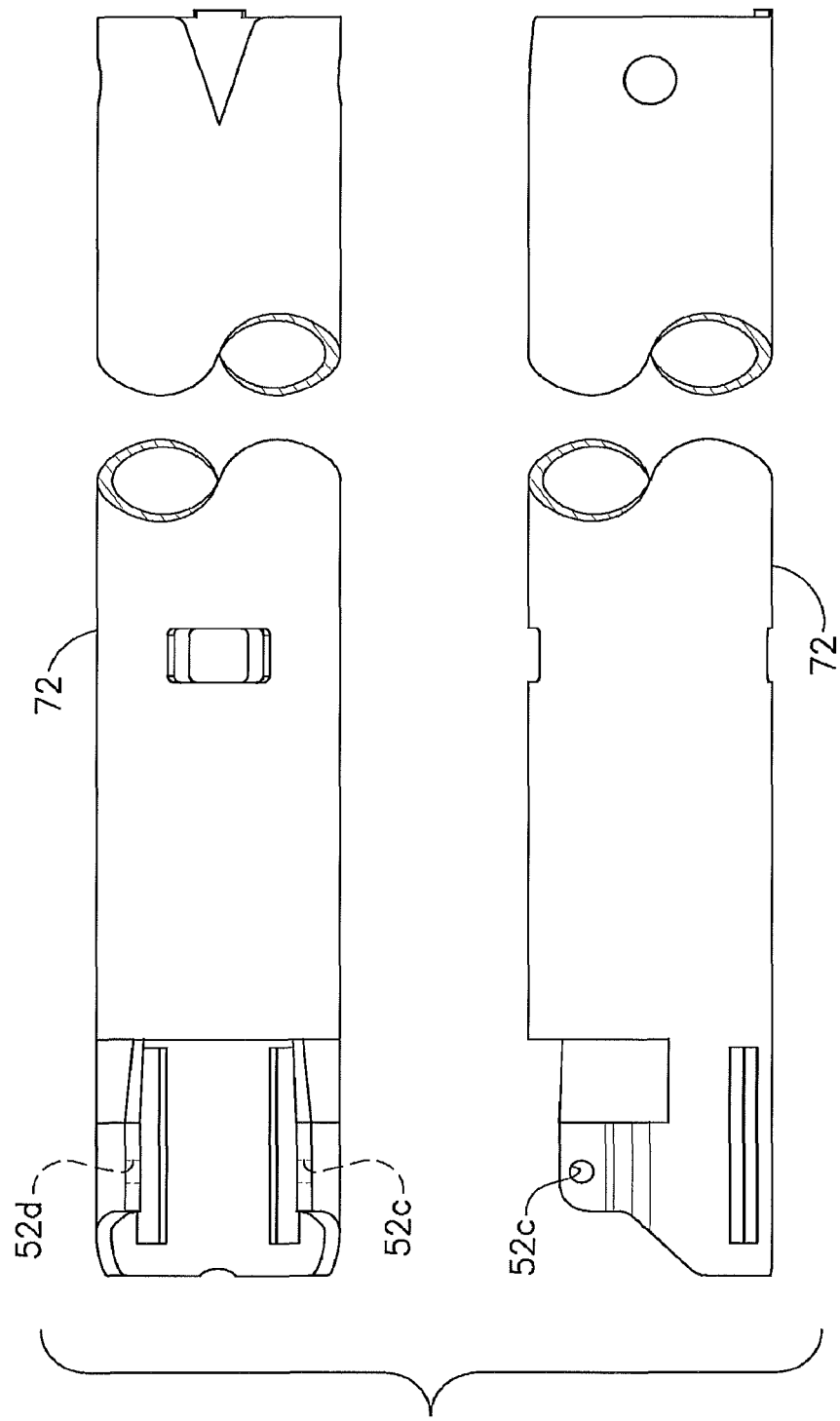
FIG. 5 is a plan view and side view of one embodiment of the outer tube of the present invention.
Figure 6:
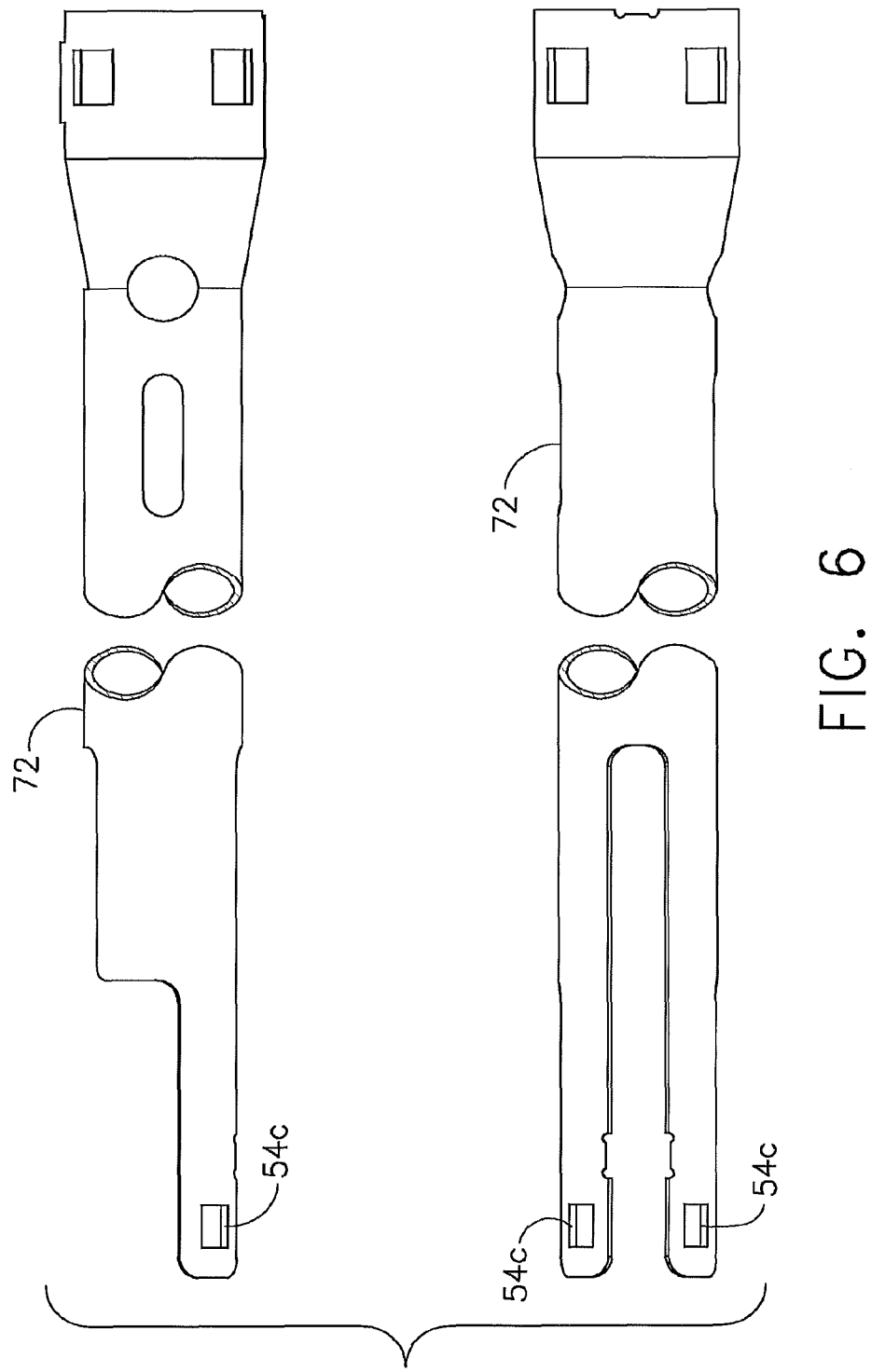
FIG. 6 is a side view and plan view of one embodiment of the inner tube of the present invention.

A second expression of a method for replacing clamp pads 58 would include one or more of the steps of: a) opening flanges on clamp arm 56 (see FIG. 4*b*); b) removing clamp pad 58 from clamp arm 56; c) removing pad insert 58*d* from clamp pad 58; d) inserting pad insert 58*d* into a clamp arm; and e) closing flanges on clamp arm 56. In this removal and replacement process, the new clamp pad 58 inserted in step "d" may be of unitary TEFLON construction, may be of composite construction, may be multiple pieces of TEFLON or composite material or may contain a pad insert or any combination thereof. Pad insert may be a new pad insert or may be a pad insert from a "used" clamp pad.

A third expression of a method for replacing a clamp pad having a base material and at-least-one pad insert material would include one or more of the steps of: a) removing the clamp pads from clamp arm 56; b) providing a new clamp pad having an opening at a proximal end thereof; c) inserting a pad insert sized to fit the opening into the opening; and d) attaching the clamp pad to the clamp arm.

Referring now to FIGS. 2, 4*a*-*b*, 5 and 6, pivotal movement of the clamp member 60 with respect to blade 79 is affected by the provision of a pair of pivot points on the clamp arm 56 that interface with the outer sheath 72 and inner tube 76 respectively. The outer sheath 72 is grounded to handle 70 through outer tube retainer 29. Clamp arm 56 is pivotally connected to outer sheath 72 via corresponding through holes 52*a* and 52*b* on clamp arm 56 and 52*c* and 52*d* on outer sheath 72. Pin 56*b* slides through holes 52*a*-*d* to secure clamp arm 56 to outer sheath 72. In one embodiment pin 56*b* is laser welded to clamp arm 56 so that pin 56*b* is fixed to clamp arm 56 and rotates relative to outer sheath 72. Any linear fastener will suffice and the invention is not limited to weld pin fastening.

Inner tube 76 translates along the longitudinal axis of outer sheath 72 and is grounded to the handle 70 through outer tube retainer 29. Legs 54*a*,*b* on clamp arm 56 engage slots 54*c* at the distal end of inner tube 76. The pivotal connection of clamp arm 56 to the inner and outer tubes 76, 72 provide more robustness to the end effector 81 and minimize failure modes due to excessive axial or torsional abuse loads. Further, the embodiment increases the effectiveness of the end effector 81 to provide clamp forces in excess of 5 lbs. Reciprocal movement of the actuating member 76, relative to the outer sheath 72 and the waveguide 80, thereby affects pivotal movement of the clamp arm 56 relative to the end-blade 79.

In one embodiment of the present invention, the inner tube 76 and outer sheath 72 are manufactured through rolled construction as is known and understood in the art. This rolled construction may result in significant cost savings over extrusion or other like manufacturing processes. Other manufacturing techniques, such as a drawn tube, are also contemplated herein.

Figure 7:
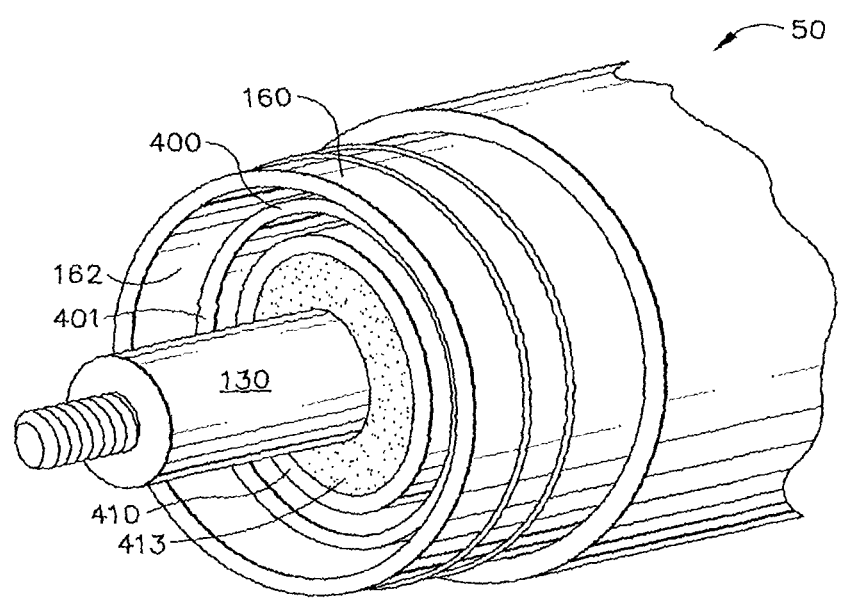
FIG. 7 is a perspective assembly view of the distal end of a handpiece assembly and electrical ring contactors.

Referring now to FIGS. 1, 2 and 7, housing 70 includes a proximal end, a distal end, and a cavity 59 extending longitudinally therein. Cavity 59 is configured to accept a switch assembly 300 and the transducer assembly 50, which interfaces with housing 68 via switch assembly 300.

Transducer 50 includes a first conductive ring 400 and a second conductive ring 410 which are securely disposed within the handpiece transducer body 50. In one expression of the current embodiment, first conductive ring 400 comprises a ring member, which is disposed between the transducer 50 and the horn 130. Preferably the first conductive ring 400 is formed adjacent to or as part of the flange member 160 within the cavity 162 and is electrically isolated from other electrical components. The first conductive ring 400 is anchored to and extends upwardly from a non-conductive platform or the like (not shown) which is formed within the transducer body 50. The first conductive ring 400 is electrically connected to the cable 22 (FIG. 1) by means of one or more electrical wires (not shown), which extend along the length of the transducer body 50 to the first conductive ring 400.

The second conductive ring 410 of the transducer 50 similarly comprises a ring member that is disposed between the transducer body 150 and the horn 130. The second conductive ring 410 is disposed between the first conductive ring 400 and the horn 130 and therefore the first and second conductive rings 400, 410 are concentric members. The second conductive ring 410 is likewise electrically isolated from the first conductive ring 400 and other electrical components contained within the transducer 50. Similar to the first conductive ring 400, the second conductive ring 410 preferably is anchored to and extends upwardly from the non-conductive platform. It will be understood that the first and second conductive rings 400, 410 are sufficiently spaced from one another so that they are electrically isolated from each other. This may be accomplished by using one or more spacers 413 disposed between the first and second conductive rings 400, 410 or between the rings 400, 410 and other members within the transducer 50. The second conductive ring 410 is also electrically connected to the cable 22 (FIG. 1) by means of one or more electrical wires (not shown), which extend along the length of the transducer 50 to the second conductive ring 410. The second conductive ring 410 is thus provided to partially define a second electrical pathway from the cable 22 to the switch mechanism 300. A suitable ultrasonic transducer 50 is Model No. HP054, sold by Ethicon Endo-Surgery, Inc. of Cincinnati, Ohio.

In one expression of the current embodiment, the distal end of transducer 50 threadedly attaches to the proximal end of waveguide 80. The distal end of transducer 50 also interfaces with switch assembly 300 to provide the surgeon with finger-activated controls on surgical instrument 100.

Figure 8A:
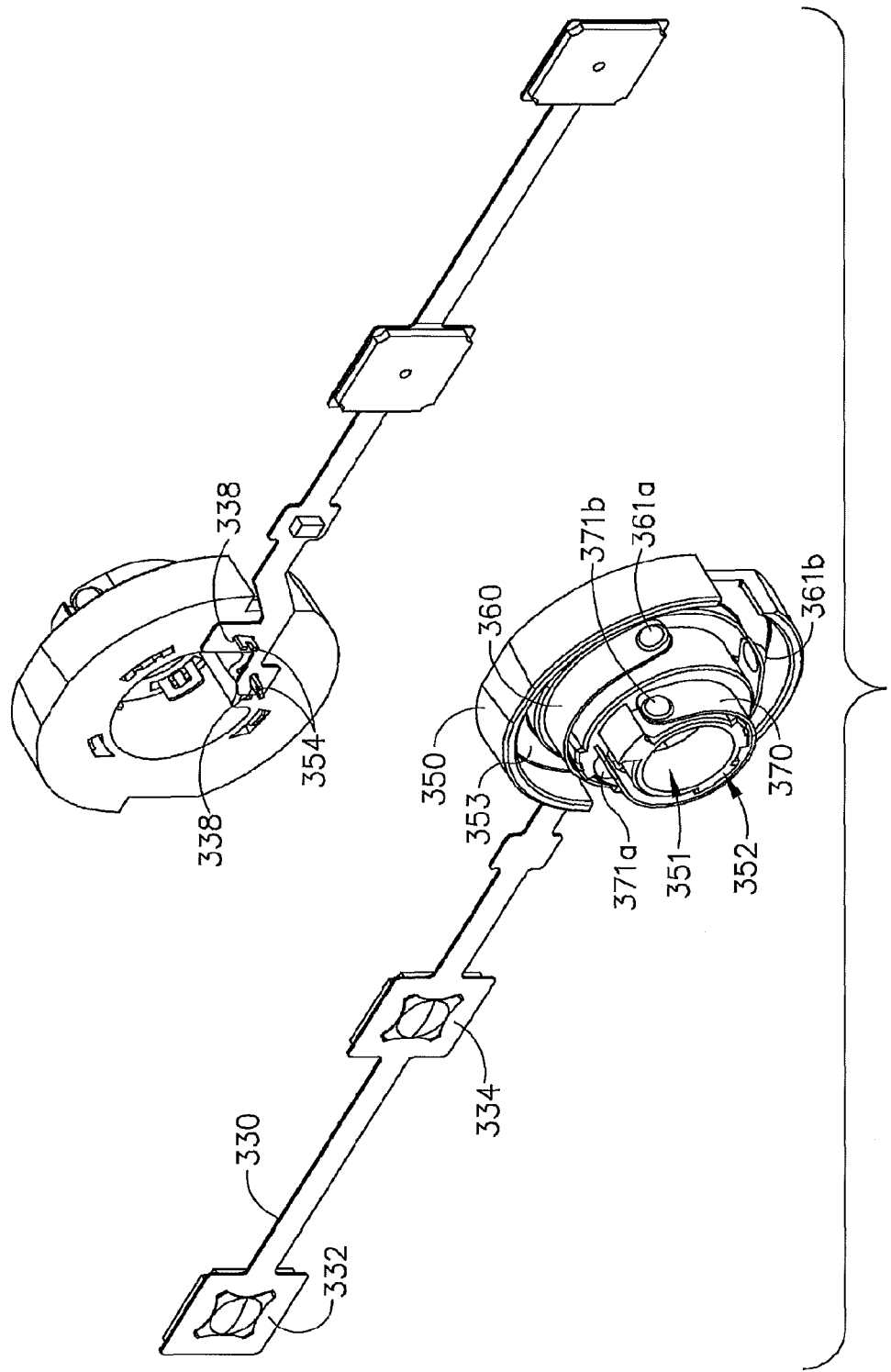
FIG. 8a is a perspective view of the front and rear sides of a connector and flexboard assembly of one embodiment of the present invention.
Figure 8B:
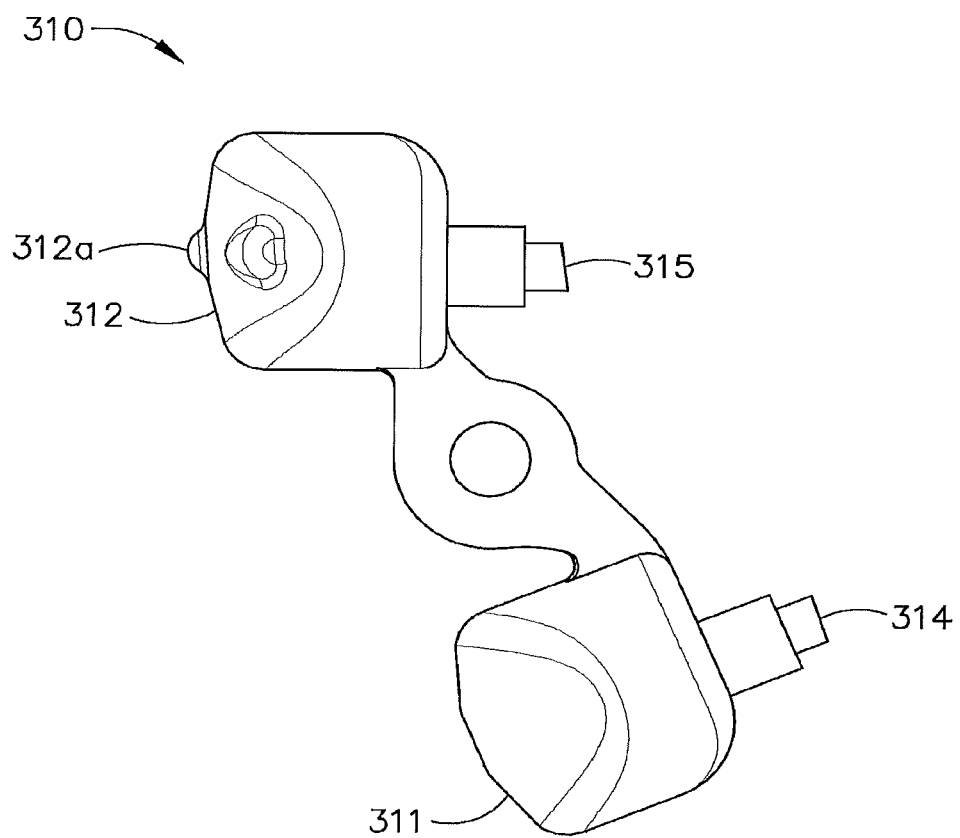
FIG. 8b is a plan view of the rocker switch of one embodiment of the present invention.
Figure 8C:
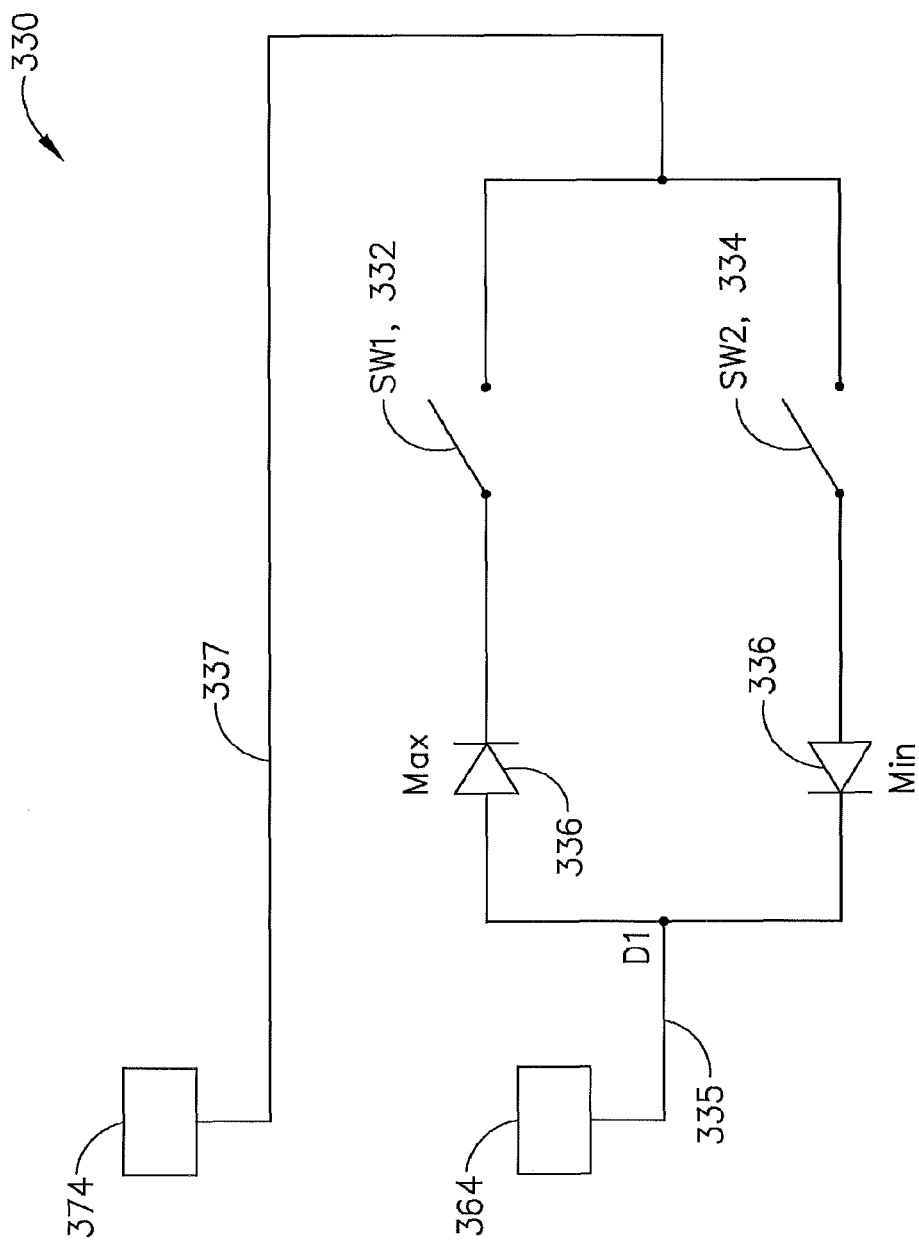
FIG. 8c is an electrical schematic of the switch circuit.

With reference now to FIGS. 8a-c, switch assembly 300 comprises a pushbutton assembly 310, a flex circuit assembly 330, a connector assembly 350, a first spring slip ring conductor 360 and a second spring slip ring conductor 370. Connector assembly 350 is generally cylindrical and is supported within handle 70 by way of corresponding supporting mounts on switch assembly 350 and housing portions 68 and 69. Connector assembly 350 defines a first cavity 353, a mounting boss 352 and a second cavity 351. Cavity 353 is sized to accept the proximal end of transducer 50, whereby horn 130 passes through cavity 351 to interface with waveguide 80. Mounting boss 352 accepts slip ring conductors 360 and 370, which in turn electrically engage ring contacts 400 and 410, respectively.

With particular reference now to FIG. 8a, slip ring conductors 360 and 370 are generally open-ended O-shaped springs that slip onto connector assembly 350. Each spring slip ring comprises two pressure point contacts (361a-b and 371a-b) that contact the respective ring conductor 400 and 410 of transducer 50. The spring tension of the slip rings 360 and 370 cause positive contact between contacts 361a-b, 371a-b and conductors 400 and 410. It is evident that the slip ring construction may allow electrical contact to be made even as the surgeon may rotate transducer 50 during use of the instrument. Posts 364 and 374 (not shown) of the respective slip rings electrically connect to the respective conductor within flex circuit 330 to complete the electrical circuit as is known and understood in the art.

A flex circuit 330 provides for the electro-mechanical interface between pushbuttons 311, 312 and the generator 30 via transducer 50. Flex circuit comprises two dome switches 332 and 334 that are mechanically actuated by depressing pushbuttons 311 or 312 respectively of corresponding pushbutton assembly 310. Dome switches 332 and 334 are electrical contact switches, that when depressed provide an electrical signal to generator 30 as shown by the electrical wiring schematic of FIG. 8d. Flex circuit 330 also comprises two diodes within a diode package 336, also illustrated in FIG. 8d. Flex circuit 330 provides conductors, 335 and 337 as is known to those in the art, that connect to slip ring conductors 360 and 370 via electrical tabs 364 and 374, respectively, which in turn provide electrical contact to ring conductors 400 and 410, which in turn are connected to conductors in cable 22 that connect to generator 30. Tabs 364 and 374 (not shown) are soldered to conductors 335 and 337.

Flex circuit 330 is partially folded and is generally fixedly attached in handle assembly 68 so that dome switches 334 and 332 interface with backing surfaces on handle assembly 69 (not shown). Backing surfaces provide a firm support for the dome switches during operation, discussed below. Dome switches 334 and 332 may be fixedly attached to backing surfaces by any convenient method, such as, an adhesive. Flex circuit is secured to connector assembly 350 via alignment pins 354 on switch assembly 350 and corresponding alignment holes 338 on flex circuit 330. As is well appreciated by one skilled in the art various electrical constructions are available to provide electrical interface between the pushbuttons and the generator, which may include molded circuits or standard wire connections.

Layered on top of flex circuit is pushbutton assembly 310, which has a corresponding saddle-shape as flex circuit 330. Pushbutton assembly 310 comprises two pushbuttons, distal pushbutton 312 and proximal pushbutton 311 which have corresponding pressure studs 315 and 314 arranged in a rocker fashion. In one embodiment, push button assembly 310 comprises a rocker style pushbutton. Other types of switches, known to the skilled artisan, are equally applicable. Rocker pushbutton assembly 310 is rotationally attached to handle 70 to provide centering action to the pushbutton assembly 310. As is readily apparent, by depressing pushbuttons 311 and 312 the corresponding pressure studs 314 and 315 depress against corresponding dome switches 334 and 332 to activate the circuit illustrated in FIG. 8c. Switches 312 and 311 are located on the ultrasonic instruments centerline so that a surgeon may operate the pushbuttons using either a left hand or a right hand. When the surgeon depresses switch 312, the generator will respond with a certain energy level, such as a maximum ("max") power setting; when the surgeon depresses switch 311, the generator will respond with a certain energy level, such as a minimum ("min") power setting, which conforms to accepted industry practice for pushbutton location and the corresponding power setting.

Alternatively, the pushbuttons may be molded into the connector assembly 350 or into the handle assembly 68 to reduce the number of components and increase the reliability of the overall device. The pushbuttons may be attached through small cantilever sections, which allow for sturdy attachment of the pushbutton to the other components, while at the same time allowing for a low force to activate the pushbuttons.

In the foregoing embodiment of the present invention, switches 311 and 312 configured in such a way to provide an ergonomically pleasing grip and operation for the surgeon. Switches may be placed in the range of the natural swing of the surgeon's index or middle fingers, whether gripping surgical instrument 100 right-handed or left handed. Referring again to FIG. 8b, in a current embodiment a series of partitions, such as ridges 312a and/or depressions or "peaks and valleys" are integrated onto the pushbutton 312. The ridges provide tactile feedback to the surgeon as to the location of the pushbuttons and whether the button represents min or max power activation. Such tactile feedback is essential to the surgeon, so the surgeon may continuously assess the surgical site, but confidently understand which pushbuttons are being activated, without the need to view the instrument 100.

Referring to FIG. 9, a surgeon's left hand is accessing instrument 100. The thumb is poised to activate trigger handle 34, and the index and middle fingers easily engage pushbutton assembly 310. The surgeon's ring finger and pinkie grasp handle 70.

In FIG. 10, a right-handed the surgeon has depressed trigger handle 34 to close clamp arm 56 against blade 79. The right forefinger can easily access pushbutton 312 to activate max power, and the left middle finger can easily access pushbutton 311b to activate min power. It can be observed that the surgeon may use the index finger to activate max power and the middle finger to activate min power. The rocker type switch allows the surgeon to rest both fingers on the min and max buttons while ensuring that both buttons are not activated simultaneously. The rocker type switch facilitates rapid change of cutting speed from max to min, back to max, etc. In previous devices, the surgeon would have to move from a foot from one pedal to another, or move his or her finger from one button to another. In some instances, the surgeon would have to look away from the operative field to locate either the desired foot pedal or desired button. The rocker switch permits the surgeon to rest two fingers on the switches during all phases of surgery obviating the need to look at or search for the desired button.

Referring to FIGS. 9 and 10, an expression of surgical instrument 100 is shown graphically illustrating a surgeon's finger placement on instrument 100. Closing of the instrument 100 is achieved by the placement of the thumb through the opening 34a in trigger handle 34 and depressing trigger handle 34. (Inserting the thumb through the opening 34a to activate trigger handle 34 is exemplary only. Surgeons with larger hands may opt to activate trigger handle 34 with the thumb on the outside of trigger handle 34 and trigger handle 34 is provided with ridges 34b to enable use of the thumb or any other finger or part of the hand on the outside of trigger handle 34 during surgery). Opening 34a is generally sized to accept different sized fingers and thumbs, a common variable as is evident depending upon the sex and size of the surgeon.

In an alternate expression of the invention, trigger handle 34 and grip handle 70 have a soft-touch molded thermo plastic elastomer liner (not shown) on their inner surfaces defining openings 34a and 68a. Plastic liner provides comfort to the surgeon and prevents finger and hand fatigue. The plastic liner also provides an enhanced gripping surface between the handles and the surgeon's thumb and fingers. This is particularly advantageous for accepting multiple digit sizes of male and female surgeons and still providing a comfortable and positive gripping surface. Plastic liner be smooth or have contours molded onto the surface of liner, such as ribs. Other contours may be bumps, and peaks and valleys. Various other shapes and interfaces are within the scope of this invention as would be obvious to one skilled in the art.

Figure 11:
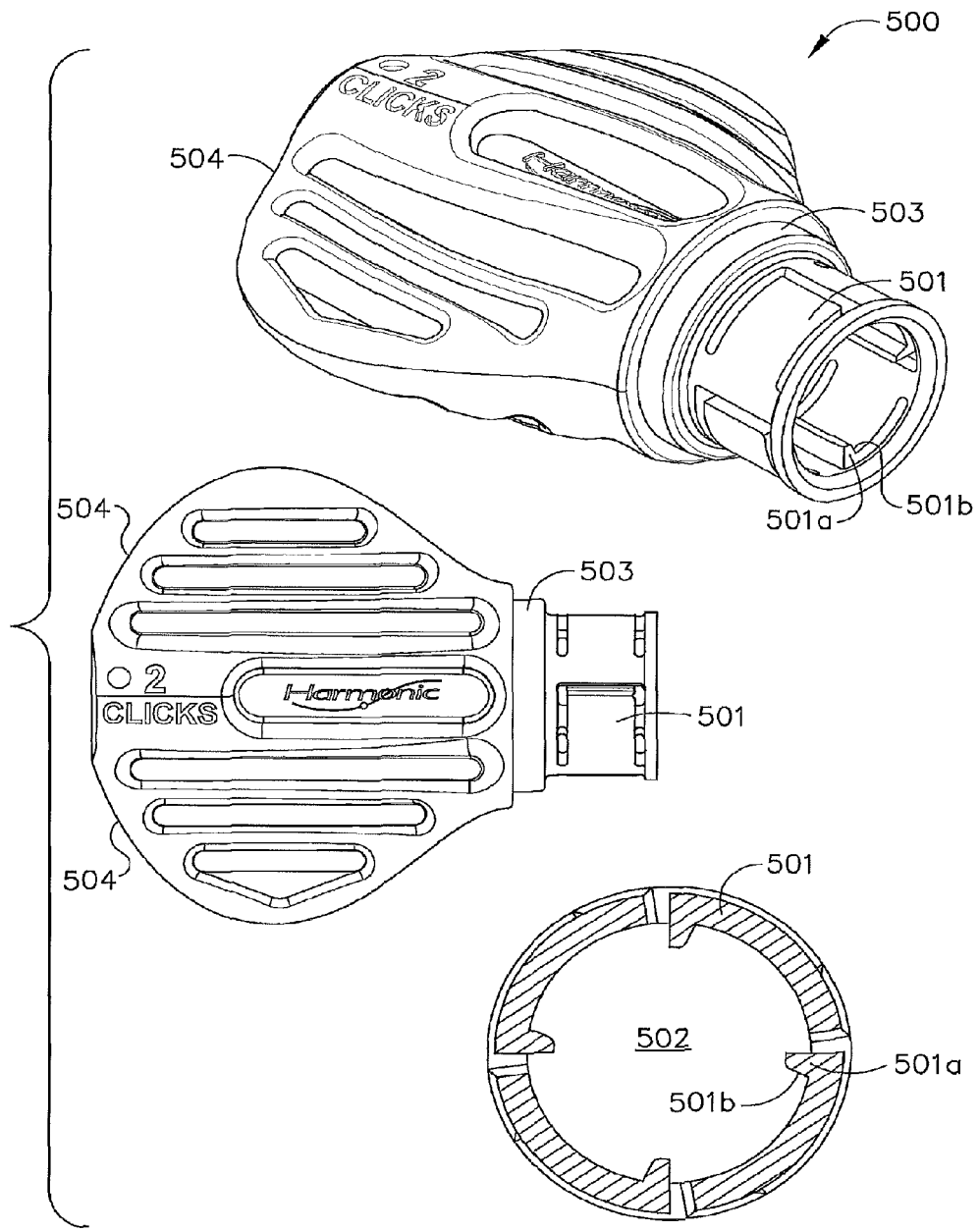
FIG. 11 is a perspective, side view and cross sectional end view of one embodiment of a torque wrench.
Figure 12:
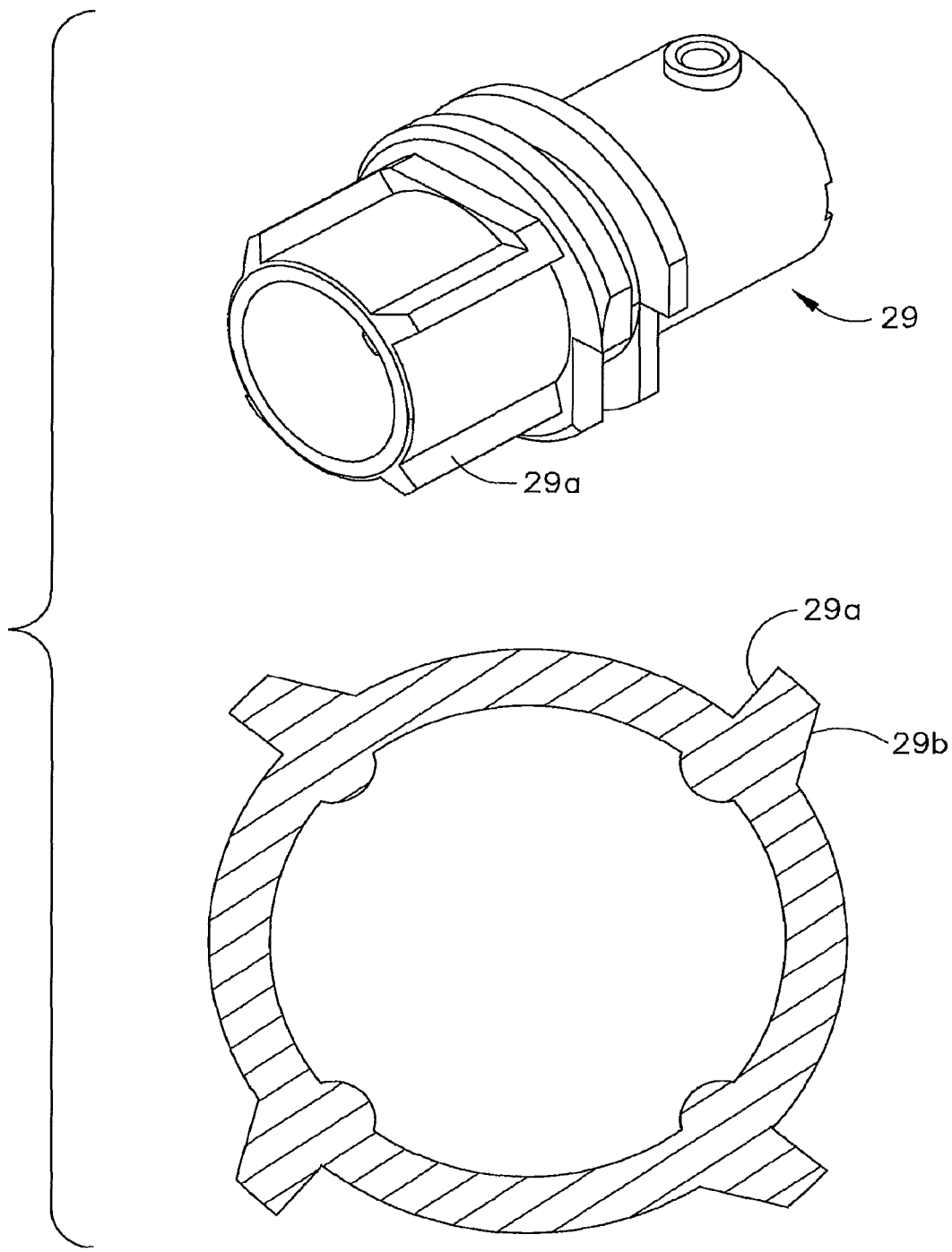
FIG. 12 is a perspective and cross sectional end view of one embodiment of an outer tube retainer of the present invention.

Referring now to FIGS. 2, 11 and 12, a one-piece torque wrench 500 is shown. The torque wrench 500, in one embodiment, is provided with cantilever arms 501 disposed in an annular fashion about the centerline of torque wrench 500. Cantilever arms 501 include teeth 501a disposed, in one embodiment, in an inward perpendicular fashion in relation to cantilever arms 501. Teeth 501a, in one embodiment of the current invention, are disposed with a cam ramp 501b at a 25° angle with respect to the perpendicular angle between arm 501 and teeth 501a.

Referring now to FIG. 12, an outer tube retainer 29 is shown. Outer tube retainer 29 includes spline gears 29a projecting in a perpendicular fashion along the outer circumference of retainer 29. Spline gears 29a include cam ramps 29b disposed at a 25.6° angle with respect to the perpendicular angle between the outer circumference of retainer 29 and spline gears 29a. Other angles of the teeth and cam ramps are contemplated and left up to the designer.

In operation, torque wrench opening 502 is aligned with outer sheath 72 and guided along substantially the entire length of sheath 72. Torque wrench lip 503 engages the distal end of handgrip 70. Cantilever teeth 501a slidably engage spline gears 29a on outer tube retainer 29. Cam ramp 501b slidably engages retainer cam ramps 29b. Clockwise annular motion or torque is imparted to torque wrench 500 through paddles 504. The torque is transmitted through arms 501 and teeth 501a to gears 29a, which in turn transmit the torque to the waveguide 80 via insulated pin 27. When a user imparts 5-12 in-lbs. of torque and holds the handpiece 50 stationary, the ramps 501b and 29b cause the arms 501 to move or flex away from the centerline of wrench 500 ensuring that the user does not over-tighten the waveguide 80 onto horn 130 (FIG. 7). When a counter-clockwise torque is applied to wrench 500 via paddles 504 (and holding the handpiece 50 stationary), the perpendicular flat sides of teeth 501a and 29a abut allowing a user to impart a torque to the interface between the waveguide 80 and horn 130 in proportion to the force applied to the paddles facilitating removal of the instrument 100 from the handpiece 50. The torque wrench 500 may be constructed from a durable plastic, such as polycarbonate or a liquid crystal polymer. It is also contemplated that the wrench 500 may alternatively be made from a variety of materials including other plastics, ceramics or metals.

In another embodiment (not shown), the paddles and cantilever arm assembly may be separate components attached by mechanical means or chemical means such as adhesives or glue.

Referring now to FIGS. 2, 5, 6 and 13, force limiting mechanism 95 provides a wave spring 94. Wave spring 94 is operationally coupled to yoke 33, which in turn is driven by trigger handle 34. Wave spring 94 generates the end effector load and maintains the consistency of the end effector load. As a result, the end effector load is more tightly controlled and component abuse load conditions are reduced. Mechanical interference or contact between trigger handle 34 and handle 70 are a safe guard against wave spring 94 being fully compressed, thereby preventing the spring material to yield and render wave spring 94 useless in subsequent clamp arm closures. As would be appreciated by one skilled in the art, the application of a mechanical stop spring force limiting system has applicability in other energy-based surgical devices (such as RF, microwave and laser) that encounter clamping forces, as well as mechanical devices, such as, clip appliers, graspers and staplers.

In one expression of the current embodiment, wave spring 94 has a spring constant about 43 pounds per inch. Wave spring 94 is preloaded to a force necessary to achieve the desired transection force, and is a function of the mechanical advantage of the clamp arm 56 coupling means and frictional losses in the device. In a second expression of the current embodiment, wave spring 94 is preloaded at about 13 pounds.

Figure 13:
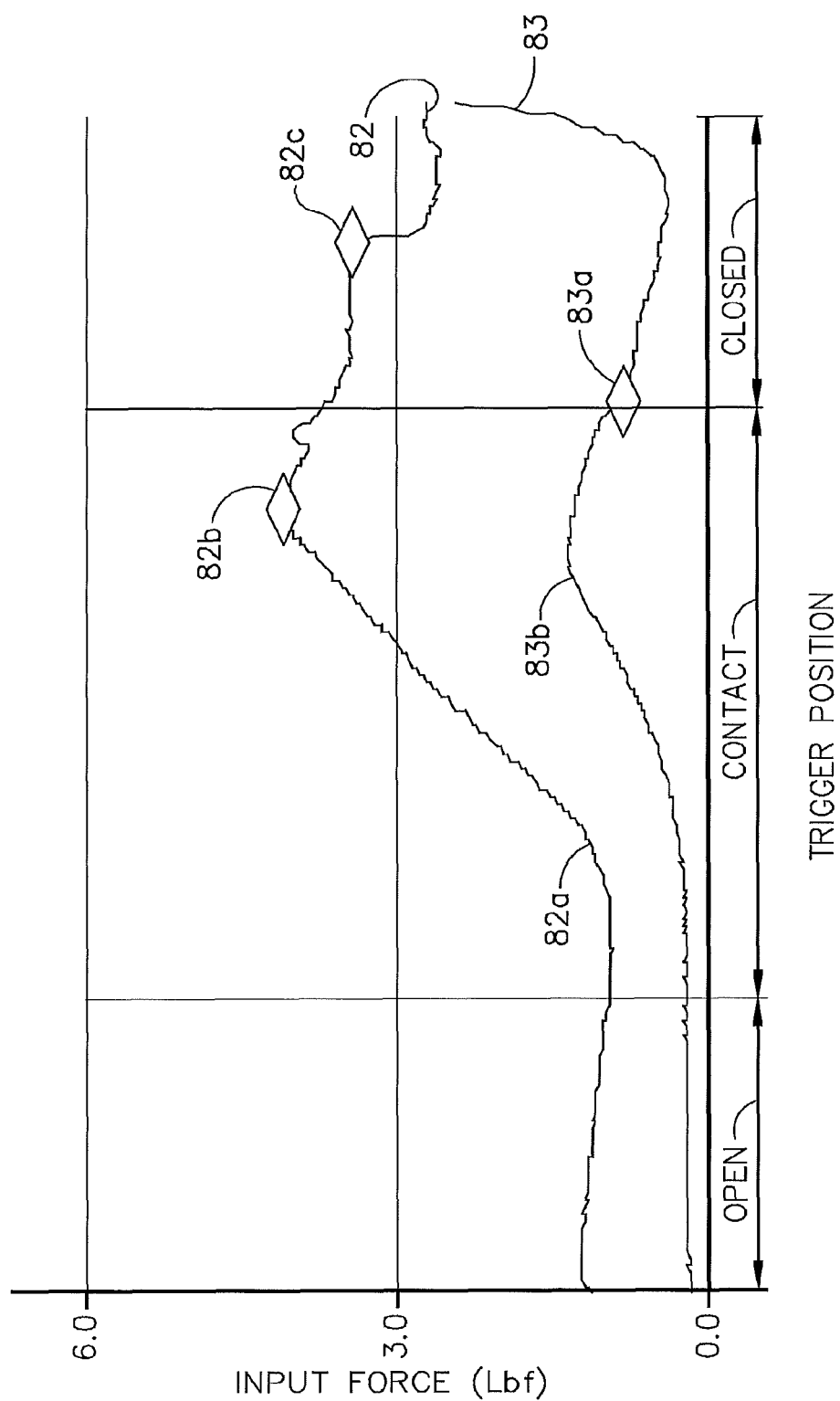
FIG. 13 is a force curve illustrating various forces as a function of the trigger position.

Referring now to FIG. 13, curve 82 illustrates trigger handle 34 force as a function of the angular rotation of trigger handle 34 for clamp arm closure and curve 83 represents trigger handle force as a function of angular rotation of trigger handle 34 for clamp arm opening. Point 82a represents the point at which yoke 33 begins to deflect or compress wave spring 94 and the force increases as trigger handle 34 is depressed further until the force reaches the preload value of wave spring 94 at inflection point 82b, and the slope of the force curve decreases. Point 82c represents trigger handle force where trigger handle 34 contacts handle 70 resulting in a mechanical stop.

In FIG. 13, curve 83 illustrates the force exerted on the trigger handle 34 by spring 12. Point 83a represents the point at which trigger handle 34 disengages from handle 70 and wave spring 94 and spring 12 both exert force against yoke 33. Point 83b represents the maximum force that trigger handle 34 exerts against a user during the opening stroke of trigger handle 34 and clamp arm 56. As can be appreciated by curves 82 and 83 in the "closed" region in FIG. 13, less force is required to maintain the trigger handle 34 in a closed position than required to achieve the closed position. This difference in forces proves advantageous during long surgical procedures where hand fatigue may be a factor. For example, a surgeon may unknowingly relax pressure on the trigger handle 34 during a long transection; with lower forces required to keep trigger handle 34 fully closed, consistent cutting and hemostasis is achieved.

Referring now to FIG. 2, surgical instrument 100 further provides for audible and tactile means for indicating to the surgeon that the trigger has reached full travel and the clamp arm 56 is applying the correct coaptation force to the tissue. Clicker 339 located in handle 70 contacts trigger handle tab 34a upon closing or opening in a momentary fashion such that trigger handle tab 34a causes clicker 339 to yield and spring back to its original position resulting in an audible and tactile "click." This is useful during protracted surgical operations or tissue transection activities when the surgeon's grip may relax, without the surgeon's knowledge, and the pressure delivered to the tissue from the clamp arm 56 may be unknowingly decreased.

Clicker 339 is generally planar and made of a flexible plastic that adequately deflects when it engages trigger handle tab 34a thereby providing an audible and/or tactile signal to the surgeon that there is full end effector 81 closure. Advantageously, tab 34a strikes and deflects clicker 339 when trigger handle 34 is rotated from the full closure position and in the opposite direction thereby providing an audible and/or tactile signal to the surgeon that full closure of end effector 81 no longer exists. As would be appreciated by the skilled artisan, the indicating means may be either tactile, audible or visual or a combination. Various types of indicators may be used including dome switches, solid stops, cantilever springs or any number of mechanical or electrical switches known to those skilled in the art. Further various means may be used to provide feedback to the surgeon, including, but not limited to, lights, buzzers, and vibratory elements.

Preferably, the ultrasonic clamp coagulator apparatus described above will be processed before surgery. First, a new or used ultrasonic clamp coagulator apparatus is obtained and if necessary cleaned. The ultrasonic clamp coagulator apparatus can then be sterilized. In one sterilization technique the ultrasonic clamp coagulator apparatus is placed in a closed and sealed container, such as a plastic or TYVEK bag. Optionally, the ultrasonic clamp coagulator apparatus can be bundled in the container as a kit with other components, including a torque wrench. The container and ultrasonic clamp coagulator apparatus, as well as any other components, are then sterilized in any conventional medical sterilization technique, such as gamma radiation, x-rays, high-energy electrons or ETO (ethylene oxide). The sterilization kills bacteria on the ultrasonic clamp coagulator apparatus and in the container. The sterilized ultrasonic clamp coagulator apparatus can then be stored in the sterile container. The sealed container keeps the ultrasonic clamp coagulator apparatus sterile until it is opened in the medical facility.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

We claim:

1. A torque wrench for coupling an ultrasonic surgical instrument to an ultrasonic transducer, the torque wrench comprising:
    a torque receiving element defining a central axis, the torque receiving element comprising two or more of gears arranged about the central axis, each gear comprising a first portion and a second portion;
    a body comprising a cantilever arm arranged annularly about the gears, the cantilever arm adapted to engage the first portions of the gear when the body is rotated in a first rotational direction about the central axis causing the cantilever arm to flex away from the central axis thereby imparting to the torque receiving element a first torque sufficient to operatively couple an ultrasonic surgical instrument to an ultrasonic transducer, and the cantilever arm engaging the second portions of the gears when the body is rotated in a second rotational direction about the central axis thereby imparting to the torque receiving element a second torque having a magnitude greater than the first torque.

2. The torque wrench of claim 1, wherein the first portions are ramped.

3. The torque wrench of claim 1, wherein the second portions are stepped.

4. The torque wrench of claim 3, wherein the stepped portions are substantially perpendicular to the central axis.

5. The torque wrench of claim 1, whereby when the body is rotated in the second rotational direction, the cantilever arm engages the second portion of one of the gears thereby imparting a non-limited torque to the torque receiving element.

6. The torque wrench of claim 1, wherein the cantilever arm comprises a distal tooth adapted to engage the gears.

7. The torque wrench of claim 1, further comprising paddles on the body.

8. The torque wrench of claim 1, wherein the torque receiving element and body define a through bore aligned with the central axis.

9. A surgical system, comprising:
    an ultrasonic surgical instrument; and
    the torque wrench of claim 1.

10. A torque wrench for coupling an ultrasonic surgical instrument to an ultrasonic transducer, the torque wrench comprising:
    a) a torque receiving element comprising a centerline and an outer surface circumscribing the centerline; and
    b) a handle comprising a cantilever arm arranged concentrically with the outer surface, the cantilever arm adapted to engage:
        i) the torque receiving element outer surface when the handle is rotated in a first direction about the centerline causing the cantilever arm to flex away from the centerline thereby imparting to the torque receiving element a limited torque sufficient to operatively couple an ultrasonic surgical instrument to an ultrasonic transducer, and ii) the torque receiving element outer surface when the handle is rotated in a second direction about the centerline thereby imparting to the torque receiving element a torque proportional to a force applied to the handle.

11. A surgical system, comprising:
an ultrasonic surgical instrument; and
the torque wrench of claim 10.

12. A torque wrench for coupling an ultrasonic surgical instrument to an ultrasonic transducer, the torque wrench comprising:
   a) a torque receiving element comprising a centerline and an outer surface circumscribing the centerline; and
   b) a handle comprising a cantilever arm arranged concentrically with the outer surface, the cantilever arm adapted to engage:
   i) the torque receiving element outer surface when the handle is rotated in a first direction about the centerline causing the cantilever arm to flex away from the centerline thereby imparting to the torque receiving element a limited torque sufficient to operatively couple an ultrasonic surgical instrument to an ultrasonic transducer, and
   ii) the torque receiving element outer surface when the handle is rotated in a second direction about the centerline thereby imparting to the torque receiving element a second torque having a magnitude greater than the limited torque.

13. A surgical system, comprising:
an ultrasonic surgical instrument; and
the torque wrench of claim 12.

* * * * *